(12) United States Patent
Ohta et al.

(10) Patent No.: US 10,197,502 B2
(45) Date of Patent: Feb. 5, 2019

(54) INFORMATION PROCESSING DEVICE, INFORMATION PROCESSING METHOD AND MEDIUM

(71) Applicant: NEC Corporation, Tokyo (JP)

(72) Inventors: Masahiko Ohta, Tokyo (JP); Jun Takada, Tokyo (JP); Hiroshi Imai, Tokyo (JP); Atsushi Hatabu, Tokyo (JP); Gaku Nakano, Tokyo (JP); Zhen Wang, Tokyo (JP); Yuzo Senda, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 15/304,484

(22) PCT Filed: Feb. 19, 2015

(86) PCT No.: PCT/JP2015/000792
§ 371 (c)(1),
(2) Date: Oct. 14, 2016

(87) PCT Pub. No.: WO2015/159469
PCT Pub. Date: Oct. 22, 2015

(65) Prior Publication Data
US 2017/0038307 A1    Feb. 9, 2017

(30) Foreign Application Priority Data

Apr. 16, 2014    (JP) .................. 2014-085029

(51) Int. Cl.
*G01B 11/14*    (2006.01)
*G01N 21/88*    (2006.01)
*G01B 11/16*    (2006.01)

(52) U.S. Cl.
CPC ......... *G01N 21/8851* (2013.01); *G01B 11/16* (2013.01); *G01N 21/88* (2013.01)

(58) Field of Classification Search
CPC ...... G01N 21/88; G01N 21/8851; G01N 3/06; G01N 27/82; G01B 11/16; G01R 31/34
See application file for complete search history.

(56) References Cited

U.S. PATENT DOCUMENTS

2009/0322373 A1\* 12/2009 Dooley ................. G01N 27/82
324/765.01

FOREIGN PATENT DOCUMENTS

| JP | 2-198306 | | 8/1990 | |
| JP | 02198306 | A * | 8/1990 | ............ G01B 11/16 |
| JP | 11-259656 | | 9/1999 | |
| JP | 11259656 | A * | 9/1999 | ............ G01N 21/88 |

(Continued)

OTHER PUBLICATIONS

International Search Report and Written Opinion dated May 26, 2015, in corresponding PCT International Application.

*Primary Examiner* — Jamil Ahmed
(74) *Attorney, Agent, or Firm* — Finnegan, Henderson, Farabow, Garrett & Dunner, L.L.P.

(57) ABSTRACT

For detecting a crack formed on a structure surface without erroneously, an information processing device that detects a crack on a structure, includes a change detection unit that detects a change in positions of at least two measurement points on the structure; and a crack detection unit that detects a crack based on the change in the positions of the measurement points detected by the change detection unit.

20 Claims, 27 Drawing Sheets

(56) References Cited

FOREIGN PATENT DOCUMENTS

| | | | |
|---|---|---|---|
| JP | 11-326225 | 11/1999 | |
| JP | 2003-35528 | 2/2003 | |
| JP | 2006-118913 | 5/2006 | |
| JP | 2006-162477 | 6/2006 | |
| JP | 2006-162548 | 6/2006 | |
| JP | 2006162548 A * | 6/2006 | ............... G01N 3/06 |
| JP | 2011-191282 | 9/2011 | |

* cited by examiner

Fig. 3
(A)
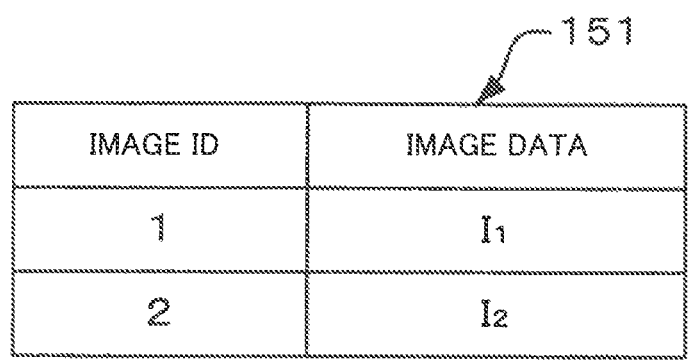
(B)
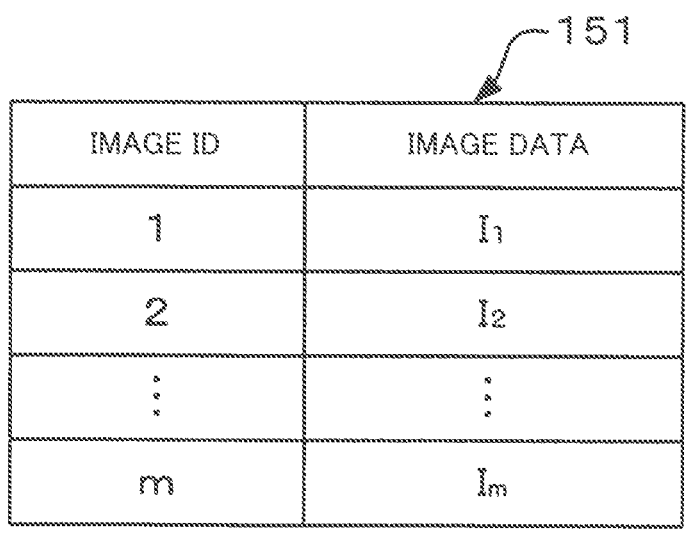

Fig. 4
(A)
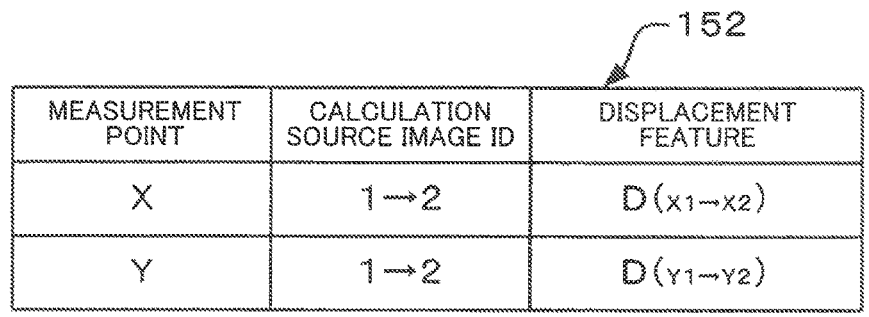
(B)
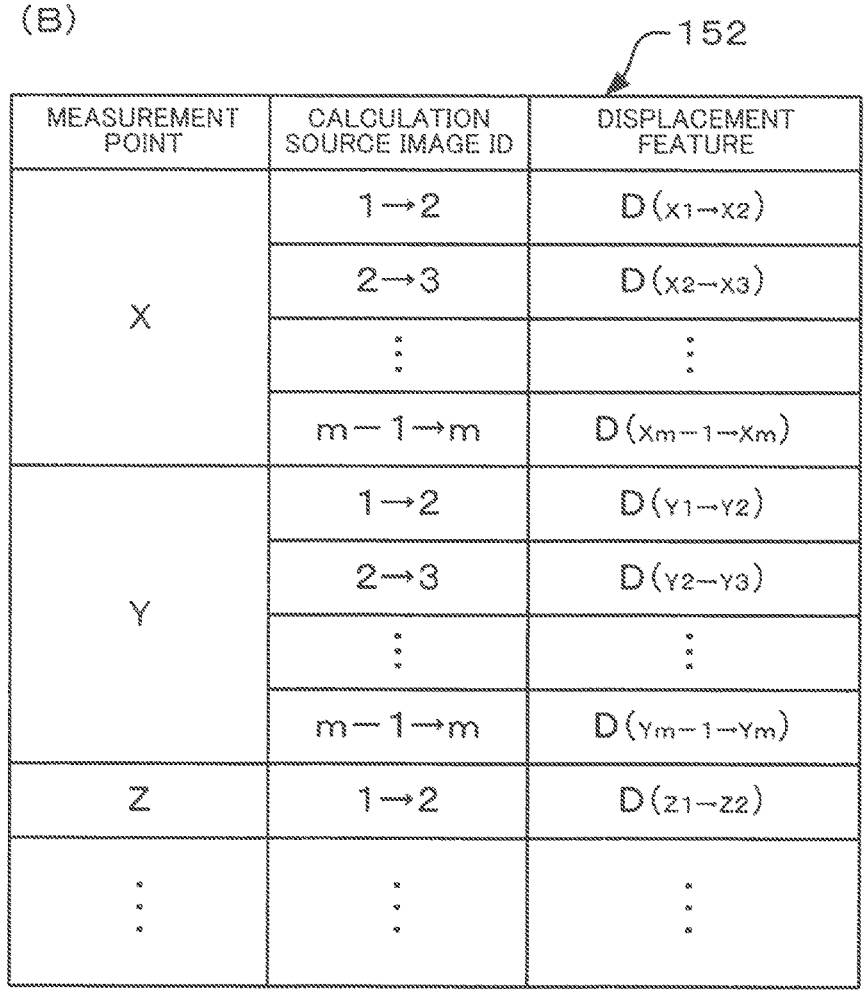

Fig. 5
(A)
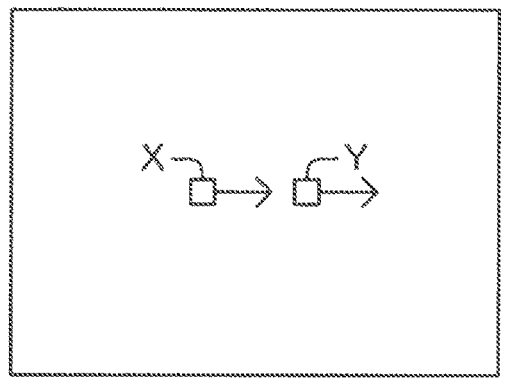
(B)
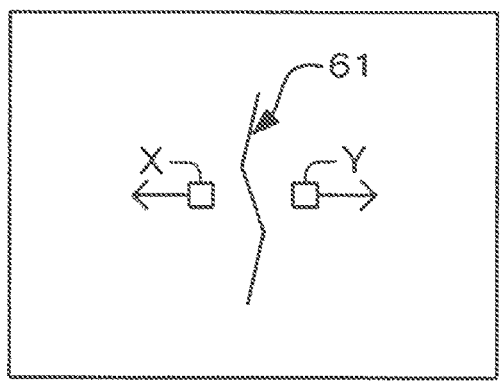
(C)
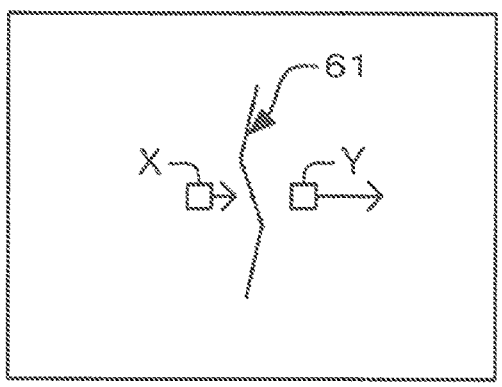

Fig. 8
(A)
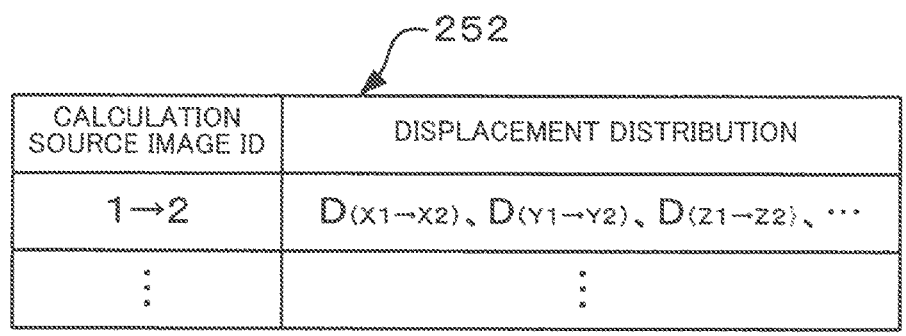
(B)
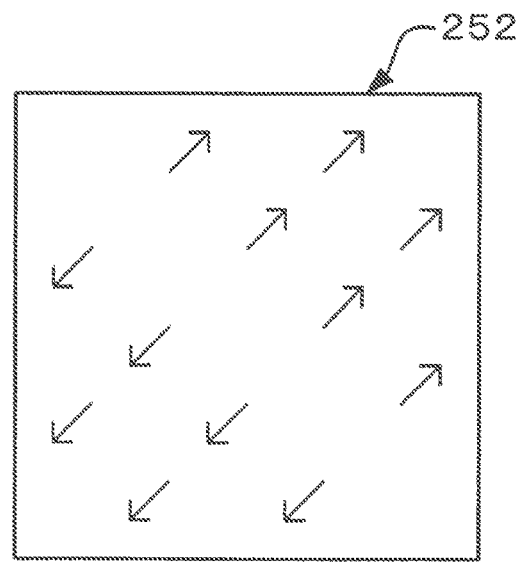

Fig. 9
(A)
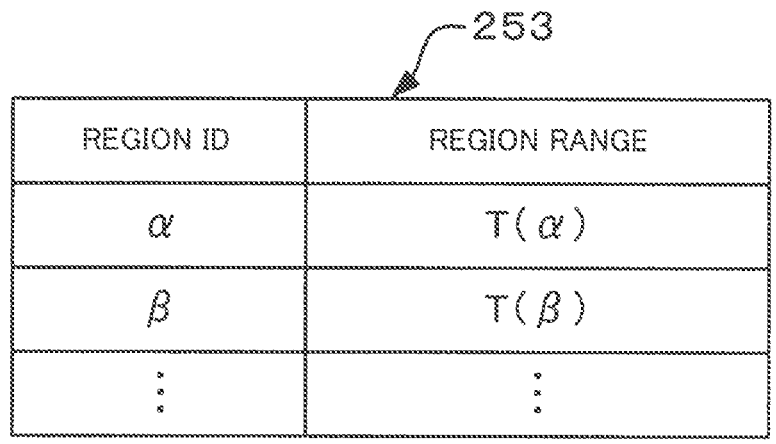
(B)
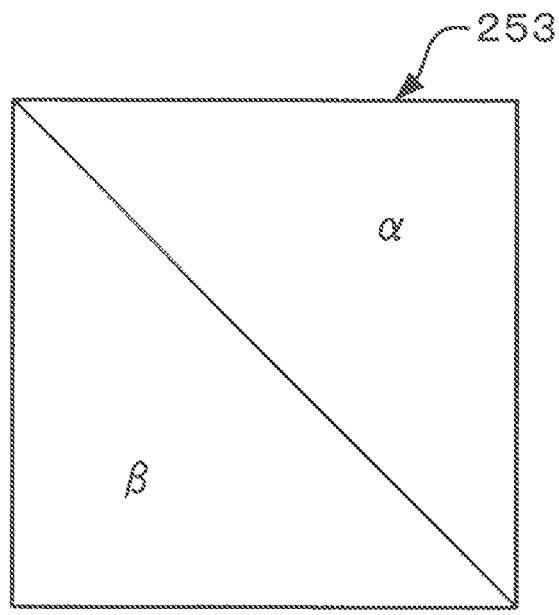

Fig. 10
(A)
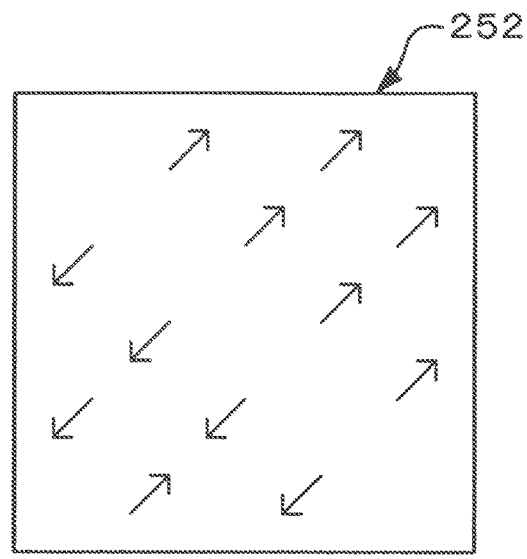
(B)
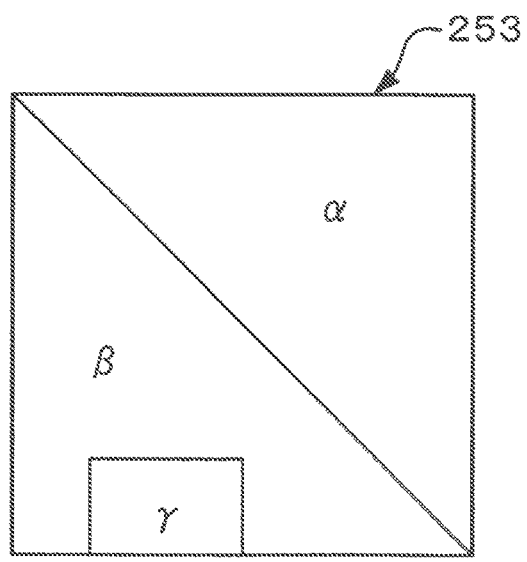

INFORMATION PROCESSING DEVICE, INFORMATION PROCESSING METHOD AND MEDIUM

CROSS-REFERENCE TO RELATED PATENT APPLICATIONS

This application is a National Stage Entry of International Application No. PCT/JP2015/000792, filed Feb. 19, 2015, which claims priority from Japanese Patent Application No. 2014-085029, filed Apr. 16, 2014. The entire contents of the above-referenced applications are expressly incorporated herein by reference.

TECHNICAL FIELD

The present invention relates to an information processing device, a program, and an information processing method for detecting a crack of a structure.

BACKGROUND ART

It has been known that, in a concrete structure such as a tunnel and a bridge, a crack formed on the surface of the structure has an influence on the soundness of the structure. Therefore, in order to accurately determine the soundness of the structure, it is necessary to accurately detect a crack.

As a method for detecting a crack, for example, there is a method for detecting a crack by visual observation. However, accuracy of detection of a crack by visual observation depends on the ability of a person who performs visual observation. Therefore, it may not be possible to accurately detect a crack according to the ability of a person who performs visual observation. As described above, the method for detecting a crack by visual observation has a problem that it depends on the ability of a person. In this regard, there have been proposed various technologies that allow for detecting a crack regardless of the ability of a person, in addition to the detection of a crack by the visual observation.

For example, a technology for binarizing an image captured by a capturing means by a predetermined threshold value and detecting an image part corresponding to a crack from the image for a structure is proposed, as a first related art to the present invention (for example, see Patent Literature 1).

Furthermore, a technology for capturing a structure by using a capturing means a plurality of times while changing an angle of a light source that lights the surface of the structure, comparing pixel values of the same measurement target parts of each image with each other, and detecting a crack image is proposed, as a second related art to the present invention (for example, see Patent Literature 2).

Furthermore, a technology for removing a low frequency component of an image obtained by capturing a structure, by using wavelet transformation, creating binary image data by removing spots and stains with small spatial variability from the surface of the structure, and detecting a crack image from the binary image data is proposed, as a third related art to the present invention (for example, see Patent Literature 3).

CITATION LIST

Patent Literature

[PLT 1] Japanese Unexamined Patent Application Publication No. 2003-35528

[PLT 2] Japanese Unexamined Patent Application Publication No. 2006-118913

[PLT 3] Japanese Unexamined Patent Application Publication No. 2006-162477

SUMMARY OF INVENTION

Technical Problem

However, in the aforementioned first to third related arts, there is a problem that a joint of installation, a tile joint, a pattern, a stain on a surface or the like similar in appearance on an image to a crack formed on the surface of a structure are erroneously detected as a crack. This is because, since the aforementioned first to third related arts detect a crack image from an image obtained by capturing a structure, it is not possible to mechanically distinguish a pattern or the like similar in appearance on an image to the crack image.

An object of the present invention is to provide an information processing device that solves the problem of erroneously detecting a pattern or the like similar in appearance on an image to a crack formed on a structure surface.

Solution to Problem

For achieving the object, an information processing device according to one aspect of the present invention is an information processing device that detects a crack on a structure. The information processing device includes:

a change detection unit that detects a change in positions of at least two measurement points on the structure; and a crack detection unit that detects a crack based on the change in the positions of the measurement points detected by the change detection unit.

An information processing method according to another aspect of the present invention is a method that detects a crack on a structure. The method includes:

detecting a change in positions of at least two measurement points on the structure; and detecting a crack based on the detected change in the positions of the measurement points.

A computer readable non-transitory medium according to another aspect of the present invention embodies a program. The program causes a computer to perform a method. The method includes:

detecting a change in positions of at least two measurement points on a structure; and detecting a crack based on the detected change in the positions of the measurement points.

Advantageous Effects of Invention

By configured as above, the present invention can provide an information processing device that detects a crack formed on a structure surface without erroneously detecting a pattern which is similar in appearance on an image to the crack.

BRIEF DESCRIPTION OF DRAWINGS

FIG. 3 is a diagram illustrating a configuration example of image information in the crack detection device according to the first exemplary embodiment of the present invention.

FIG. 4 is a diagram illustrating a configuration example of displacement feature information in the crack detection device according to the first exemplary embodiment of the present invention.

FIG. 5 is a diagram for explaining crack detection processing in the crack detection device according to the first exemplary embodiment of the present invention.

FIG. 8 is a diagram illustrating a configuration example of displacement distribution information in the crack detection device according to the second exemplary embodiment of the present invention.

FIG. 9 is a diagram illustrating a configuration example of region information in the crack detection device according to the second exemplary embodiment of the present invention.

FIG. 10 is a diagram for explaining region division processing in the crack detection device according to the second exemplary embodiment of the present invention.

DESCRIPTION OF EMBODIMENTS

Next, exemplary embodiments of the present invention will be described in detail with reference to the drawings.

First Exemplary Embodiment

Figure 1:
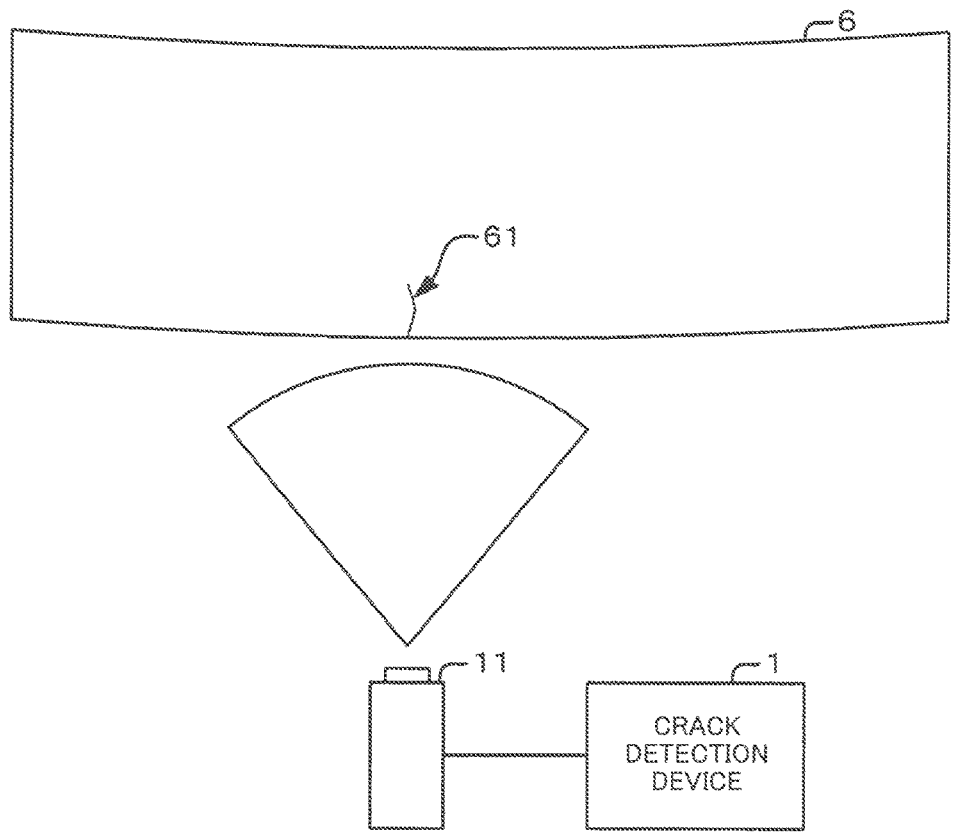
FIG. 1 is a diagram for explaining an outline of a crack detection device according to a first exemplary embodiment of the present invention.

Referring to FIG. 1, a crack detection device 1 according to a first exemplary embodiment of the present invention, by using an image of a structure 6 (a tunnel, a bridge and the like) which is captured by an image capturing unit 11, has a function of detecting a crack 61 formed on a structure 6. In general, it is known that various influences such as load and wind generally result in a change of the width of the crack 61 formed on the structure 6. However, this attribute is utilized only for dealing with the crack 61 after it is found by a certain method, and not for finding the crack 61. The crack detection device 1 according to the first exemplary embodiment of the present invention is a device that detects the crack 61 formed on the aforementioned structure 6 by using a change of the width of the crack 61 formed on the structure 6.

Figure 2:
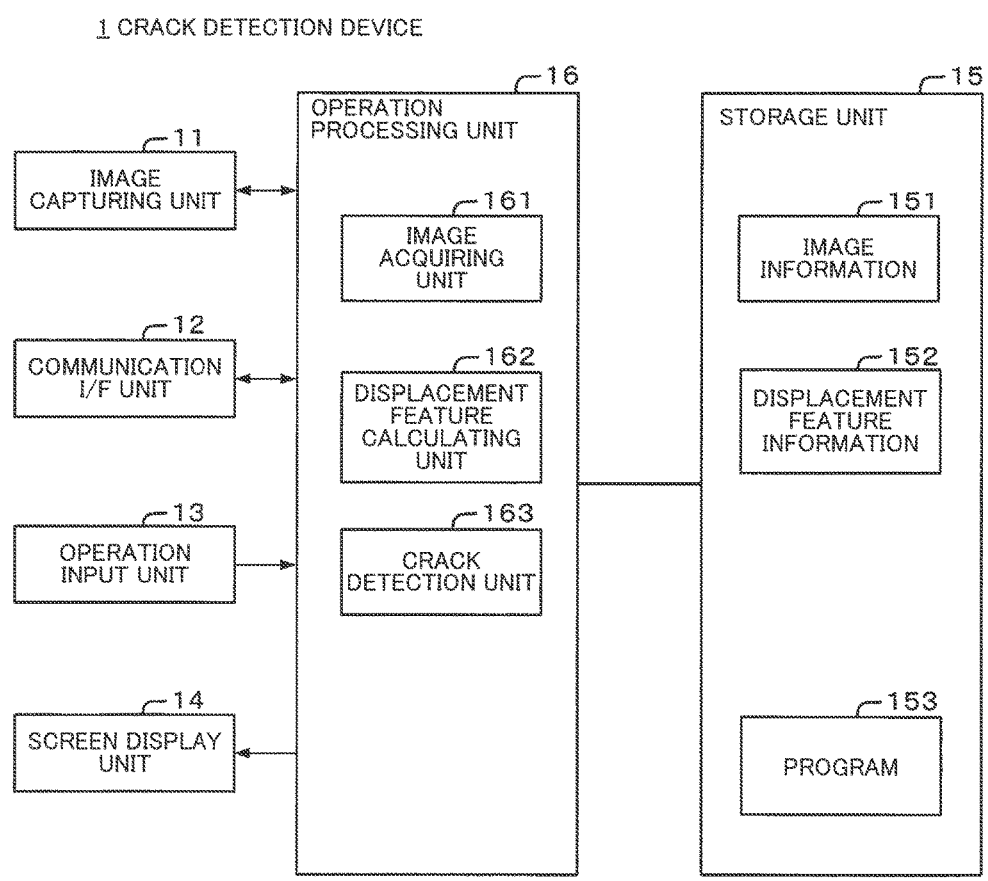
FIG. 2 is a block diagram illustrating a configuration of the crack detection device according to the first exemplary embodiment of the present invention.

Referring to FIG. 2, the crack detection device 1 has the image capturing unit 11, a communication I/F unit 12, an operation input unit 13, a screen display unit 14, a storage unit 15, and an operation processing unit 16 as main elements.

The image capturing unit 11 includes an image capturing device such as a digital camera and a digital video camera and has a function of acquiring image data by capturing the structure 6 from which is a target of detecting a crack. In the present exemplary embodiment, the image capturing unit 11 captures the same range (a range which is a target of detecting a crack) of the structure 6 serving as an object at least twice at a time interval decided in advance for example. In addition, the image capturing unit 11 may continuously capture the structure 6, thereby acquiring time-series image data.

The communication I/F unit 12 includes a dedicated data communication circuit and has a function of performing data communication with various devices connected via a communication line.

The operation input unit 13 includes an operation input device such as a keyboard and a mouse and has a function of detecting an operation of an operator and outputting the detected operation to the operation processing unit 16.

The screen display unit 14 includes a screen display device such as an LCD (Liquid Crystal Display) and a PDP (Plasma Display Panel). The screen display unit 14 has a function of displaying various pieces of information, such as information of the crack 61 formed on the structure 6, on a screen in response to an instruction from the operation processing unit 16.

The storage unit 15 is a storage device such as a hard disk and a memory. The storage unit 15 has a function of storing processing information required for various types of processing in the operation processing unit 16 and a program 153. The program 153 is a program which is read and executed by the operation processing unit 16 to realize various processing units. The program 153 is read in advance from an external device (not illustrated) or a storage medium (not illustrated) via a data input/output function of the communication I/F unit 12 and the like, and is stored in the storage unit 15. Main information to be stored in the storage unit 15 includes image information 151 and displacement feature information 152.

The image information 151 is information indicating image data of a range which is a target of detecting the crack 61, which is acquired by capturing the structure 6 by the image capturing unit 11. FIG. 3 (A) is a configuration example of the image information 151. Referring to FIG. 3 (A), the image information 151 stores image data, and image IDs which are information for identifying the image data. For example, the first row of FIG. 3 (A) indicates that image data "$I_1$" is stored in association with an image ID "1".

In addition, the image information 151 stores image data in association with a capturing range. For example, in (A) of FIG. 3, the image data "$I_1$" is stored in association with the image Identification (ID) "1" and image data "$I_2$" is stored in association with an image ID "2". The image data "$I_1$" and the image data "$I_2$" are image data acquired by capturing the same range by the image capturing unit 11.

Furthermore, the image information 151 stores image data, for example, in the order from an image captured earlier (from an image acquired earliest). That is, in the image information 151, image IDs are assigned to the image data in the order from the older. For example, (A) of FIG. 3 indicates that the image data "$I_2$" corresponding to the image ID "2" is captured after the image data "$I_1$" corresponding to the image ID "1" had been captured. Furthermore, when the image capturing unit 11 acquires time-series image data, the image information 151 can store the time-series image data, for example, in an order from the older one as illustrated in (B) of FIG. 3. Furthermore, the image information 151 may include information indicating a time at which image data is acquired.

The displacement feature information 152 is information that is generated from data of images captured in the same range at different times and indicates temporal changes in positions of arbitrary regions (measurement points) in the image data. The displacement feature information 152 includes information indicating a temporal change in positions of at least two arbitrary regions.

FIG. 4 (A) is a configuration example of the displacement feature information 152. Referring to FIG. 4 (A), the displacement feature information 152 has measurement points, calculation source image IDs, and displacement features. That is, for each measurement point for which temporal position change is measured, the displacement feature information 152 stores calculation source image IDs, which indicate image data becoming a calculated object of displacement features, in association with corresponding displacement features (displacement directions and displacement quantities), which indicate changes in the positions of the measurement points. For example, the first row of FIG. 4 (A) indicates a displacement feature "$D_{(x1\_x2)}$" calculated using image data with an image ID "1" and image data with an image ID "2" (that is, image data "$I_1$" and "$I_2$").

In addition, the displacement feature information 152 can store displacement features corresponding to respective time-series image data, for example, as illustrated in FIG. 4 (B). Furthermore, as illustrated in FIG. 4 (B), the displacement feature information 152 can store displacement features of two or a plurality of measurement points.

The operation processing unit 16 has a microprocessor such as a MPU and a peripheral circuit thereof, and has a function of making the aforementioned hardware and the program 153 cooperate with each other, and implementing various processing units, by reading the program 153 from the storage unit 15 to execute it. Main processing units implemented by the operation processing unit 16 include an image acquiring unit 161, a displacement feature calculating unit 162 (a measurement-point-position-change detection means), and a crack detection unit 163.

The image acquiring unit 161 has a function of acquiring image data from the image capturing unit 11 and storing the acquired image data in the image information 151 of the storage unit 15. That is, the image acquiring unit 161 acquires the image data from the image capturing unit 11. Then, the image acquiring unit 161 stores the acquired image data in the image information 151 of the storage unit 15.

The displacement feature calculating unit 162 has a function of reading the image information 151 from the storage unit 15, detecting a temporal position change in of an arbitrary region (the measurement point) in the image data, and calculating a displacement feature. Concretely, the displacement feature calculating unit 162 according to the present exemplary embodiment detects a temporal position change of region around the measurement point by applying a region-based image search method typified by a template matching method or a digital image correlation method to the read image data, and calculates a displacement feature. For example, the displacement feature calculating unit 162 reads the image data "$I_1$" and the image data "$I_2$" from the image information 151 of the storage unit 15. Then, the displacement feature calculating unit 162 tracks which region in the image data "$I_2$" corresponds to an arbitrary region $X_1$ in the image data "$I_1$". In this way, the displacement feature calculating unit 162 detects that the position of the arbitrary region $X_1$ in the image data "$I_1$" is moved to the position of a region $X_2$ in the image data "$I_2$". Then, based on the detection result, the displacement feature calculating unit 162 calculates a displacement feature including a displacement direction and a displacement quantity. Alternatively, the displacement feature calculating unit 162 may be configured to detect point-based displacement based on an arbitrary measurement point. In this case, the displacement feature calculating unit 162 can use an image feature point on such as a luminance gradient, a corner, and an edge or a local feature such as a SIFT (Scale Invariant Feature Transform) as a feature point of an image serving as a measurement point, detect a temporal position change of the measurement point, and calculate a displacement feature.

Thereafter, the displacement feature calculating unit 162 associates the calculated displacement feature with an image ID indicating the image data from which the displacement feature is calculated, and stores the result in the storage unit 15 as the displacement feature information 152. It should be noted that the displacement feature calculating unit 162 calculates displacement features with respect to at least two measurement points.

The crack detection unit 163 has a function of reading the displacement feature information 152 from the storage unit 15 and detecting the crack 61 formed between measurement points. For example, the crack detection unit 163 reads a displacement feature "$D_{(X1\_X2)}$" for a measurement point X and a displacement feature "$D_{(Y1\_Y2)}$" for a measurement point Y. Then, when a predetermined relation decided in advance exists between the aforementioned two read displacement features "$D_{(X1\_X2)}$" and displacement feature "$D_{(Y1\_Y2)}$", the crack detection unit 163 detects that there is the crack 61 between the measurement point X and the measurement point Y.

Here, displacements of the measurement points X and Y when a strain occurs in the structure 6 by a certain stress. In this case, in general, for example, as illustrated in FIG. 5 (A), displacement features of the measurement point X and the measurement point Y are expected to be similar values (approximately the same quantity in the same direction). On the other hand, as described above, the width of the crack 61 formed on the structure 6 is changed by an influence of a load, wind, and other various influences. Therefore, when the crack 61 exists between the measurement point X and the measurement point Y, the displacement feature of the measurement point X and the displacement feature of the measurement point Y are largely affected by an influence of a change in the crack width. As a consequence, for example, as illustrated in FIG. 5 (B), the displacement directions of the measurement point X and the measurement point Y are different from each other. In other cases, as illustrated in FIG. 5 (C), a large difference may occur in displacement quantities of the measurement point X and the measurement point Y. As described above, when the crack 61 exists between the measurement point X and the measurement point Y, the displacement feature of the measurement point X and the displacement feature of the measurement point Y are largely different from each other due to an influence of a change in the crack width. In this regard, when the relation between the displacement feature of the measurement point X and the displacement feature of the measurement point Y satisfies predetermined conditions such as a difference in displacement directions and a large difference in displacement quantities as described above, the crack detection unit 163 detects the crack 61 between the measurement point X and the measurement point Y or suggest a probability.

After the detection of the crack 61, the crack detection unit 163 displays on the screen display unit 14 that the crack 61 is detected. At this time, the crack detection unit 163, for example, may be configured to display the detected crack 61 on the image data from which is a target for detecting crack.

The above is the description about the configuration of the crack detection device 1.

Figure 6:
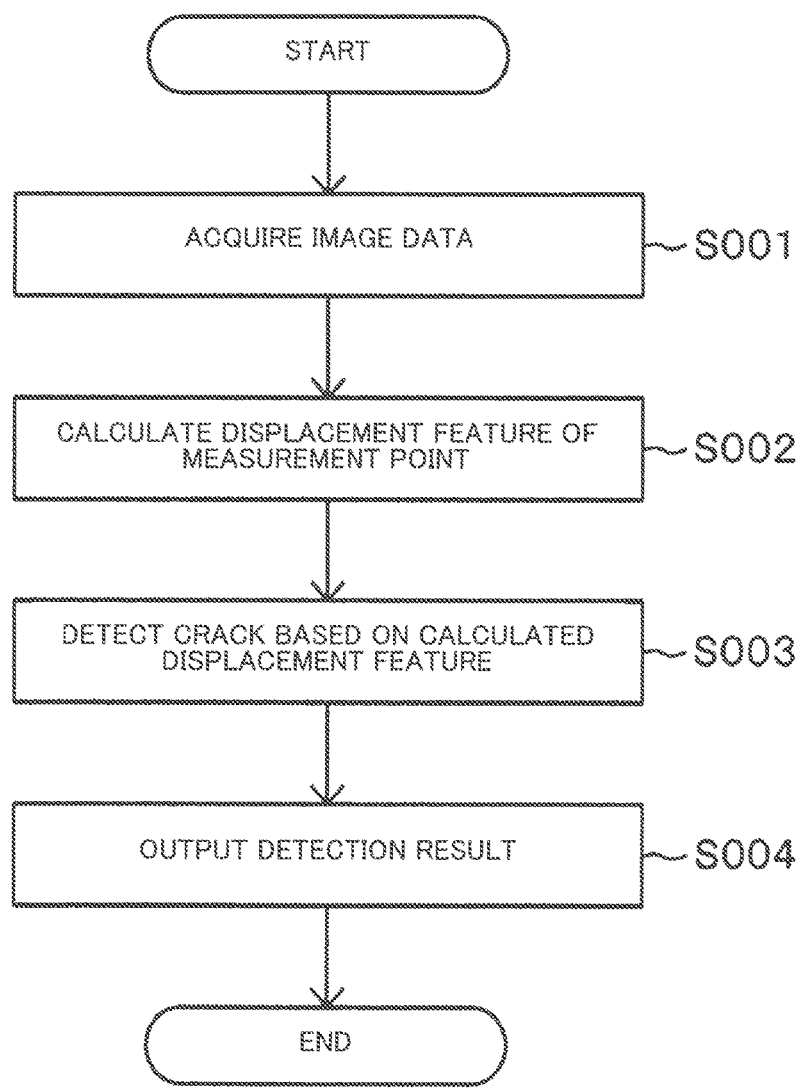
FIG. 6 is a flowchart illustrating an operation of the crack detection device according to the first exemplary embodiment of the present invention.

Next, an operation of the crack detection device 1 will be described. FIG. 6 is a flowchart illustrating the operation of the crack detection device 1 according to the present exemplary embodiment. Hereinafter, with reference to FIG. 6, the operation of the crack detection device 1 will be described.

Referring to FIG. 6, the image capturing unit 11 captures the structure 6 to acquire image data (step S001). The image data acquired by the image capturing unit 11 is stored in the storage unit 15 as the image information 151 via the image acquiring unit 161.

Next, the displacement feature calculating unit 162 detects a temporal position change of an arbitrary region (a measurement point) of the image data based on the image data stored in the image information 151 of the storage unit 15, and calculates a displacement feature (step S002). Then, the displacement feature calculating unit 162 stores the calculated displacement feature in the storage unit 15 as the displacement feature information 152. It should be noted that the displacement feature calculating unit 162 calculates displacement features for at least two measurement points.

Subsequently, the crack detection unit 163 detects the crack 61 based on the displacement feature of each of the measurement points stored in the displacement feature information 152 of the storage unit 15 (step S003). Thereafter, the crack detection unit 163 displays on the screen display unit 14 that the crack 61 is detected (step S004).

As described above, the crack detection device 1 according to the present exemplary embodiment includes the displacement feature calculating unit 162 and the crack detection unit 163. By such a configuration, the crack detection unit 163 can detect that the crack 61 exists, based on the relations with each of displacement features of measurement points, which are calculated by the displacement feature calculating unit 162. As described above, the width of the crack 61 is changed by various influences. Therefore, a displacement feature of measurement point around the crack 61 is affected by an influence of a change in the crack width. In contrast, to a pattern or the like similar in appearance on an image, the above feature that the crack 61 has does not apply. Therefore, by detecting the crack 61 based on the relations of displacement features of measurement points, it is possible to detect the crack 61 formed on the surface of the structure 6 without erroneously detecting a pattern or the like similar in appearance on an image to the crack 61.

In addition, the crack detection device 1 according to the present exemplary embodiment can also calculate a displacement speed, a displacement acceleration and the like as a displacement feature by using time-series image data. The crack detection device 1 may be configured to detect the crack 61 based on a displacement feature including a displacement speed, a displacement acceleration and the like. Furthermore, the crack detection device 1 may be configured to detect the crack 61 based on a displacement direction alone or may be configured to detect the crack 61 based on a displacement alone.

Furthermore, in the present exemplary embodiment, the timing at which the image capturing unit 11 acquires image data is not particularly limited. However, for example, by configuring the image capturing unit 11 to acquire image data at timings before and after the generation of stress for the structure 6, it is possible to more accurately detect the crack 61. As described above, the width of the crack 61 is changed in response to a load and the like. Therefore, by acquiring image data at timings before and after the generation of stress, that is, at timings before and after a change in the width of the crack 61, it is possible to more accurately detect the crack 61.

Furthermore, the crack detection device 1 can be configured to detect that there is a crack between two measurement points based on the relations of the changes in the positions of the two measurement points and the relations of the changes in the positions of measurement points around the two measurement points. For example, the crack detection device 1 detects the probability that a crack 61 exists between the two points satisfying the aforementioned predetermined condition. Thereafter, from the displacements of the two points, which the probability of presence of a crack 61 are detected, and between them, and other measurement points around the two points, the crack detection device 1 determines whether there is a continuity in the displacements of the two points detected the probability of the crack 61 in the relation with the other measurement points. For example, the crack detection device 1 determines that there is a continuity when it is determined that the displacement of the two points detected a probability of a crack 61 is a series of relations with the other measurement points (for example, when it is determined that a certain regularity is observed in the relations among displacements of measurement points including the two points, for example, such that the greater the distance of a measurement point from a certain reference point, the larger the displacement quantity becomes). On the other hand, the crack detection device 1 determines that the displacements of the two points detected the probability of a crack 61 is discontinuous in the relations with the displacements of the other measurement points when the relations of the displacements of the other measurement points nearby greatly differ from the relations of the displacements of the two points detected the probability of a crack 61. An example would be a case in which there is a large difference in the displacement directions or the displacement quantities of the displacements of the two points detected the probability of a crack 61, even when there is observed a certain regularity such that the greater the distance of a measurement point from a certain point, the larger the displacement quantity becomes. When there is a continuity, the crack detection device 1 determines that there is no crack 61 between the two points detected the probability of a crack 61. On the other hand, when the displacements of the two points detected the probability of a crack 61 are discontinuous in the relations with the displacements of the other measurement points, the crack detection device 1 determines that there is a crack 61 between the two points detected the probability of the crack 61. The crack detection device 1 can be configured to perform such determination. By configuring the crack detection device 1 as above, it is possible to prevent an erroneous detection in which a part having a gentle change of displacement feature, for example, which is a center portion of a bridge and the like at a time of stress being generated, is detected a crack 61. In addition, the crack detection device 1 may be configured to detect the crack 61 after initially determining continuity. That is, the crack detection device 1 can be configured not to detect a crack 61 between measurement points at which there is observed a continuous change. Furthermore, the crack detection device 1 may be configured to detect a crack 61 between adjacent measurement points having a discontinuous relation in positional changes among measurement points having discontinuous changes.

In the present exemplary embodiment, the case in which the crack detection device 1 uses the image capturing unit 11 as a position measurement sensor has been described. However, the implementation of the present invention is not limited to the aforementioned cases. The crack detection device 1, for example, may be configured to calculate a displacement feature by using a contact type sensor such as a contact type acceleration sensor and a strain gage, a vibration measurement sensor such as a laser Doppler vibration meter, or a displacement measurement sensor such as a laser displacement meter.

Furthermore, the crack detection device 1, for example, may be configured to limit a capturing region by using a ROI (Region of Interest) after detecting a crack width change region from a wide area capturing image.

Furthermore, as the structure 6 from which the crack detection device 1 detects the crack 61, for example, a concrete structure is supposed. However, a target from which the crack detection device 1 detects the crack 61 is not limited to the concrete structure. The crack detection device 1, for example, may be used for detecting a crack formed on a structure such as a steel structure and a wooden article.

Next, a second exemplary embodiment of the present invention will be described in detail with reference to the drawings.

Second Exemplary Embodiment

In the second exemplary embodiment, a description will be provided for a crack detection device 2 that calculates a displacement distribution by calculating displacement features of a plurality of measurement points. The crack detection device 2 divides a crack detection target range into a plurality of regions based on the calculated displacement distribution and detects the crack 61 at a boundary of the divided regions.

Figure 7:
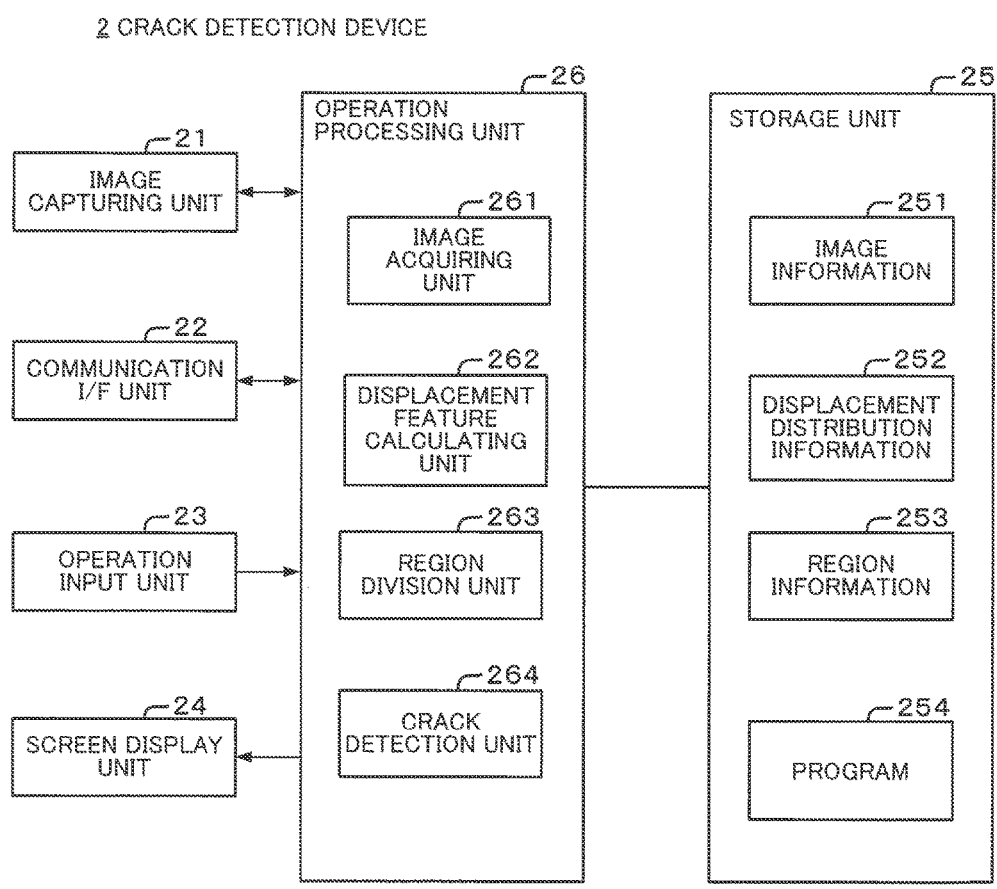
FIG. 7 is a block diagram illustrating a configuration of a crack detection device according to a second exemplary embodiment of the present invention.

Referring to FIG. 7, the crack detection device 2 according to the present exemplary embodiment has an image capturing unit 21, a communication I/F unit 22, an operation input unit 23, a screen display unit 24, a storage unit 25, and an operation processing unit 26 as main elements. The image capturing unit 21, the communication I/F unit 22, the operation input unit 23, and the screen display unit 24 have the same functions as those of the image capturing unit 11, the communication I/F unit 12, the operation input unit 13, and the screen display unit 14 of the crack detection device 1 according to the first exemplary embodiment. Therefore, a description thereof will be omitted.

The storage unit 25 is a storage device such as a hard disk and a memory. The storage unit 25 has a function of storing processing information required for various types of processing in the operation processing unit 26 and a program 254. The program 254 is a program which is read and executed by the operation processing unit 26 to realize various processing units. The program 254 is read in advance from an external device (not illustrated) or a storage medium (not illustrated) via a data input/output function of the communication I/F unit 22 and the like, and is stored in the storage unit 25. Main information to be stored in the storage unit 25 includes image information 251, displacement distribution information 252, and region information 253.

The image information 251 is information indicating image data, which is acquired by capturing the structure 6 by the image capturing unit 11, of a range which is a target of detecting a crack is detected. The configuration of the image information 251 is the same as that of the image information 151 of the crack detection device 1 according to the first exemplary embodiment of the present invention illustrated in FIG. 2 (see FIG. 3 for the configuration example of the image information 151). Therefore, a description thereof will be omitted.

The displacement distribution information 252 is information which is generated from the data of images, which are captured of the same range at different times, and indicates a distribution of displacements in the image data of a predetermined range. FIG. 8 (A) is a configuration example of the displacement distribution information 252. Referring to FIG. 8 (A), the displacement distribution information 252 stores image IDs indicating image data of a displacement distribution calculation source and a displacement distribution which is a collection of displacement features of measurement points in the predetermined range of the image data. For example, the first row of FIG. 8 (A) indicates the displacement distribution (the displacement features "$D_{(X1-X2)}$", "$D_{(Y1-Y2)}$", "$D_{(Z1-Z2)}$", . . . , of measurement points) which is calculated by using image data of an image ID "1" and image data of an image ID "2" (that is, image data "$I_1$" and "$I_2$"). When the aforementioned displacement distribution is displayed in the predetermined range of the image data, FIG. 8 (B) is obtained for example. Furthermore, the displacement features of the measurement points constituting the displacement distribution of the displacement distribution information 252 are assumed to be associated with positional information of the measurement points.

The region information 253 is information which is generated based on the displacement distribution and proximity between the positions of the measurement points and indicates the range of regions. Concretely, in the region information 253 according to the present exemplary embodiment, a region is defined as a range indicating continual measurement points similar to around ranges and the region is stored in association with a region ID identifying regions and a region range which is a range of region. FIG. 9 (A) is a configuration example of the region information 253. Referring to FIG. 9 (A), the region information 253 stores a region range, which is information indicating the range of region, and a region ID indicating information for identifying region range. For example, the first row of FIG. 9 (A) indicates that the range corresponding to the region ID "α" is "T (α)". In addition, for example, when regions are generated based on the displacement distribution as illustrated in FIG. 8 (B), the regions are divided into a region α and a region β at a boundary of discontinuous displacement features in FIG. 8 (B), as illustrated in (B) of FIG. 9.

The operation processing unit 26 has a microprocessor such as a MPU and a peripheral circuit thereof, and has a function of making the aforementioned hardware and the program 254 cooperate with each other, and implementing various processing units, by reading the program 254 from the storage unit 25 to execute it. Main processing units implemented by the operation processing unit 26 include an image acquiring unit 261, a displacement feature calculating unit 262, a region division unit 263, and a crack detection unit 264.

The image acquiring unit 261 has a function of acquiring image data from the image capturing unit 21 and storing the acquired image data in the image information 251 of the storage unit 25. That is, the image acquiring unit 261 has a function similar to that of the image acquiring unit 161 of the crack detection device 1 according to the first exemplary embodiment of the present invention.

The displacement feature calculating unit 262 has a function of reading the image information 251 from the storage unit 25 and calculating a distribution of displacements in a predetermined range of image data. Concretely, the displacement feature calculating unit 262 respectively calculates a displacement feature of each of measurement points in the predetermined range of the image data by applying a region-based image search method typified by a template matching method or a digital image correlation method to the read image data, and calculates a displacement distribution which is a distribution of displacements. For example, the displacement feature calculating unit 262 reads the image data "$I_1$" and the image data "$I_2$" from the image information 251 of the storage unit 25. Then, the displacement feature calculating unit 262 tracks which respective measurement points in a predetermined range of the image data "$I_1$" corresponds to a region belong in the image data "$I_2$", and calculates respective displacement features. Thereafter, the displacement feature calculating unit 262 calculates a displacement distribution, which is a distribution of displacements, based on the respective displacement features. Alternatively, the displacement feature calculating unit 262 may be configured to detect point-based displacement as arbitrary measurement points. In this case, the displacement feature calculating unit 262 can use an image feature point such as a luminance gradient, a corner, and an edge or a local feature such as a SIFT (Scale Invariant Feature Transform) as a feature point of an image as a measurement point, detect a temporal change in a position of the measurement point, and calculate a displacement feature.

Thereafter, the displacement feature calculating unit 262 associates the calculated displacement distribution with an image ID indicating image data for calculating the displacement distribution, and stores the result in the storage unit 25 as the displacement distribution information 252.

The region division unit 263 has a function of reading the displacement distribution information 252 from the storage unit 25 and dividing a range indicated by the displacement distribution into a plurality of regions. Concretely, the region division unit 263 determines a region indicating continuous displacement features similar to around regions as one region, and divides the range indicated by the displacement distribution. That is, based on displacement features at respective measurement points, the region division unit 263 divides a range indicated by a displacement distribution between (at the boundary between) the measurement points having discontinuous displacement features (for example, greatly different displacement directions or displacement quantities). Furthermore, the region division unit 263 performs region division based on the positions of the respective measurement points.

For example, the region division unit 263 reads the displacement distribution illustrated in FIG. 8 (B) from the displacement distribution information 252 of the storage unit 25. Then, based on the displacement distribution and the proximity of positions of the measurement points, the region division unit 263 divides a range indicated by the displacement distribution. Concretely, the region division unit 263 divides a range in such a manner that a range containing measurement points having similar to around ranges and continuous displacement features is treated as one region. As a result, as illustrated in FIG. 9 (B), the region division unit 263 divides the range indicated by the displacement distribution into, for example, the region α and the region β, at the boundary of discontinuous displacement features.

Thereafter, the region division unit 263 stores the result obtained by dividing the range indicated by the displacement distribution in the storage unit 25 as the region information 253. That is, the region division unit 263 associates the range of the divided regions with regions IDs for identifying the regions and stores the result in the storage unit 25 as the region information 253.

As described above, based on the displacement distribution and the proximity of the positions of the measurement points, the region division unit 263 divides the range indicated by the displacement distribution. Therefore, for example, when there are similar displacement features at remote positions as illustrated in FIG. 10 (A), the region division unit 263 does not regard a range having the similar displacement features at the remote positions as the same region, and divides the range into different regions. That is, the region division unit 263, for example, divides the range indicated by the displacement distribution as illustrated in FIG. 10 (B).

Figure 11:
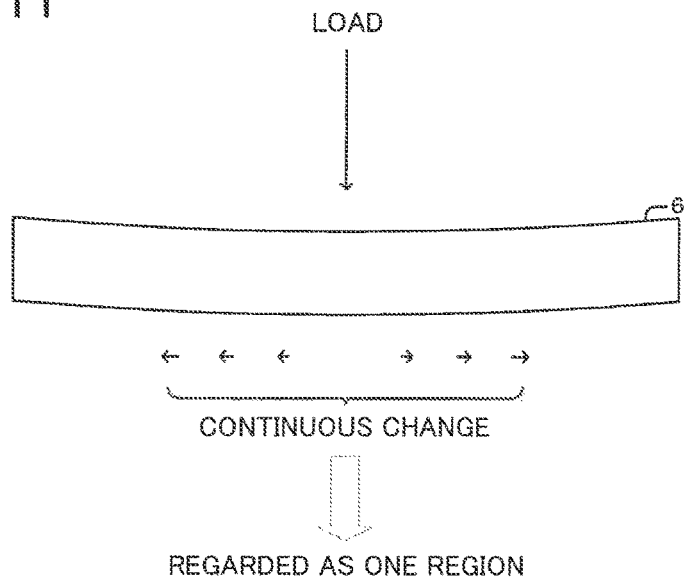
FIG. 11 is a diagram for explaining region division processing in the crack detection device according to the second exemplary embodiment of the present invention.

Furthermore, as described above, the region division unit 263 divides a range in such a manner that a range indicating measurement points having similar to around ranges and continuous displacement features is treated as one region. Therefore, for example, as illustrated in FIG. 11, when respective displacement features of measurement points have a continuous change even when including different displacement directions, the region division unit 263 determines the range having the continuous change as one region. In this way, for example, the region division unit 263 determines a range having a gradual continuous change in the structure 6, such as a center portion of a bridge when a certain load (external force) is applied, as one region.

The crack detection unit 264 has a function of reading the region information 253 from the storage unit 25 and detecting a crack 61 based on the read region information 253. For example, the crack detection unit 264 reads information indicating that the range indicated by the displacement distribution is divided into the region α and the region β (see FIG. 9 (B)). Then, the crack detection unit 264 detects that there is a crack 61 at the boundary between the region α and the region β.

A displacement distribution when strain is generated on the structure 6 by certain stress will be discussed. In general, it is expected that a homogeneous structure with no cracks will yield a displacement distribution having continuous change. On the other hand, strain and stress concentrate on a crack 61 formed on the structure 6. Accordingly, the width of the crack 61 is changed by an influence by the concentration of these strain and stress. Therefore, when the crack 61 is formed, since the width of the crack 61 is changed, a displacement distribution change occurring in the structure becomes discontinuous. That is, when the displacement distribution change is discontinuous, it is considered that the crack 61 is formed. In this regard, the crack detection unit 264 detects the crack 61 at the boundary (a part showing a discontinuous change) between regions having a continuous change.

After detecting the crack 61, the crack detection unit 264 displays on the screen display unit 24 that the crack 61 is detected. At this time, the crack detection unit 264, for example, may be configured to make the detected crack 61 be displayed on image data (or for example, on a displacement distribution) which is a target of detecting the crack 61.

So far, the configuration of the crack detection device 2 has been described.

Figure 12:
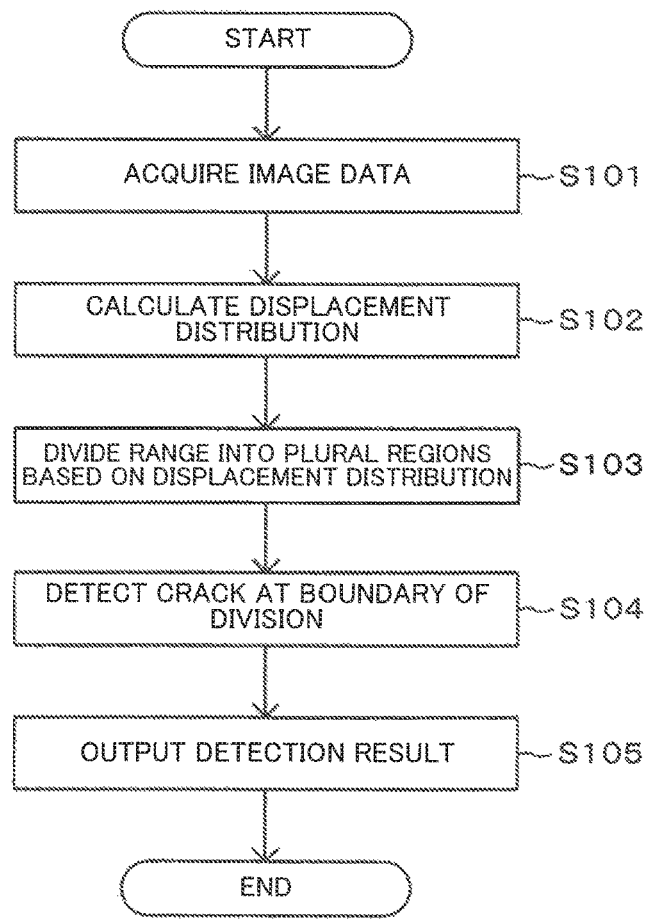
FIG. 12 is a flowchart for explaining an operation of the crack detection device according to the second exemplary embodiment of the present invention.

Next, an operation of the crack detection device 2 will be described. FIG. 12 is a flowchart illustrating the operation of the crack detection device 2 according to the present exemplary embodiment. Hereinafter, with reference to FIG. 12, the operation of the crack detection device 2 will be described.

Referring to FIG. 12, the image capturing unit 21 captures the structure 6 to acquire image data (step S101). The image data acquired by the image capturing unit 21 is stored in the storage unit 25 as the image information 251 via the image acquiring unit 261.

Next, the displacement feature calculating unit 262 calculates a displacement distribution based on the image data stored in the image information 251 of the storage unit 25 (step S102). Concretely, the displacement feature calculating unit 262 calculates the displacement distribution by applying a region-based image search method typified by a template matching method or a digital image correlation method to the read image data. Then, the displacement feature calculating unit 262 stores the calculated displacement distribution in the storage unit 25 as the displacement distribution information 252.

Subsequently, the region division unit 263 divides a range indicated by the displacement distribution into a plurality of regions based on the displacement distribution stored in the displacement distribution information 252 of the storage unit 25 and the proximity of positions of measurement points (step S103). Concretely, the region division unit 263 divides a range indicated by displacement distribution in such a manner that a range indicating measurement points having similar to around ranges and continuous displacement features is treated as one region. Then, the region division unit 263 stores the division result in the storage unit 25 as the region information 253.

Thereafter, the crack detection unit 264 detects the crack 61 based on the division result stored in the region information 253 of the storage unit 25. That is, the crack detection unit 264 detects the crack 61 at the boundary between regions in which ranges having continuous change are collected to one region (step S104). Then, the crack detection unit 264 displays on the screen display unit 24 that the crack 61 is detected (step S105).

As described above, the crack detection device 2 according to the present exemplary embodiment has the displacement feature calculating unit 262, the region division unit 263, and the crack detection unit 264. By such a configuration, based on a displacement distribution calculated by the displacement feature calculating unit 262, the region division unit 263 can divide a range indicated by the displacement distribution into a plurality of regions in such a manner that a range indicating continuity of displacement features is treated as one region. Then, based on the region division result of the region division unit 263, the crack detection unit 264 can detect the crack 61 existing in the boundary between the regions. As described above, the width of the crack 61 is changed by various influences. Therefore, around the crack 61, displacement features are discontinuous by an influence of the change in the width of the crack (for example, a displacement direction or a displacement quantity may differ). In contrast, a pattern or the like similar in appearance on an image to the crack 61 does not possess the same characteristics as the crack 61. Therefore, by dividing the range in such a manner that a range indicating continuity of displacement features is treated as one region and the crack 61 is detected at the boundary between the divided regions, it is possible to detect the crack 61 formed on the surface of the structure 6 without erroneously detecting a pattern or the like similar in appearance on an image to the crack 61.

It should be noted that, in (the region division unit 263 of) the crack detection device 2 according to the present exemplary embodiment, the range is divided in such a manner that a range indicating continuity of displacement features is treated as one region. However, the condition for dividing the range indicating the displacement distribution is not limited to the aforementioned case. For example, the region division unit 263 may be configured to divide a range in such a manner that ranges having similarity in displacement features is treated as one region regardless of the continuity of displacement features. In such a case, the crack detection unit 264 can be configured to detect the crack 61 based on a displacement feature of each region subjected to the region division. Concretely, the crack detection unit 264, for example, can be configured to detect the crack 61 at the boundary of regions which differ in displacement direction or the boundary of regions which greatly differ in displacement quantity. Furthermore, it is known that a radial stress distribution and a strain distribution are generated at an end portion of a crack. Therefore, the crack detection unit 264 may be configured to determine the crack 61 when a radial distribution of displacement features is found with the center of the distribution at an end of the boundary.

Furthermore, the crack detection device 2 may be configured to calculate a displacement speed, a displacement acceleration and the like as displacement features by using time-series image data.

Furthermore, the crack detection device 2 may be configured to calculate displacement distributions among image data acquired in time series and detect the crack 61 with respect to the respective displacement distributions.

Furthermore, in the present exemplary embodiment, the timing at which the image capturing unit 21 acquires image data is not particularly limited. However, for example, by configuring the image capturing unit 21 so as to acquire image data at timings before and after the generation of stress, it is possible to more accurately detect the crack 61.

Furthermore, the crack detection device 2, for example, may be configured to limit a capturing region by using a ROI (Region of Interest) after detecting a crack width varied region from a wide area capturing image.

Furthermore, as the structure 6 from which the crack detection device 2 detects the crack 61 may, for example, be a concrete structure. However, a target from which the crack detection device 2 detects the crack 61 is not limited to the concrete structure. The crack detection device 2, for example, may be used for detecting a crack formed on a structure such as a steel structure and a wooden article.

Next, a third exemplary embodiment of the present invention will be described in detail with reference to the drawings.

Third Exemplary Embodiment

In the third exemplary embodiment, a description will be provided for a structure soundness evaluation device 3 that calculates a displacement of the opening (width) of the crack 61 detected by the crack detection device 2 described in the second exemplary embodiment and evaluates the soundness of the structure 6 based on the displacement of the opening of the crack 61.

Figure 13:
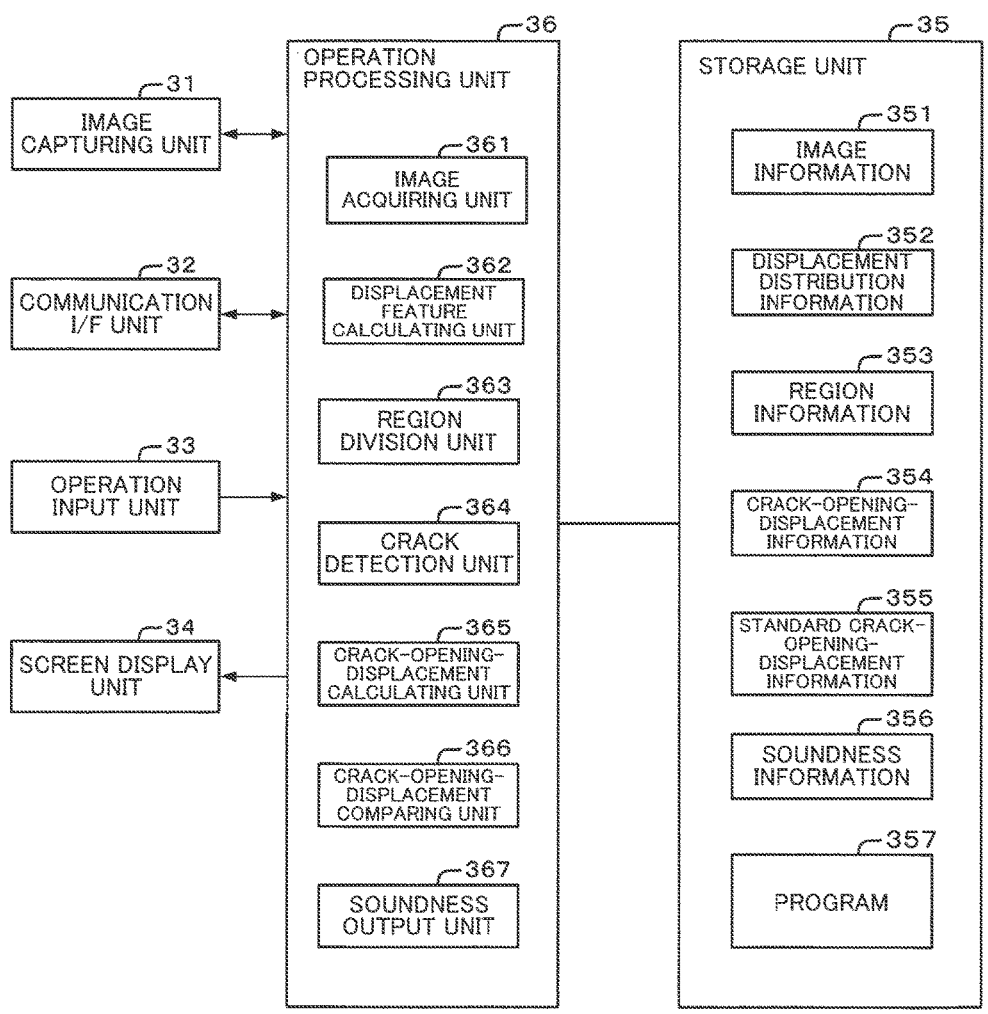
FIG. 13 is a block diagram illustrating a configuration of a structure soundness evaluation device according to a third exemplary embodiment of the present invention.

Referring to FIG. 13, the structure soundness evaluation device 3 according to the present exemplary embodiment has an image capturing unit 31, a communication I/F unit 32, an operation input unit 33, a screen display unit 34, a storage unit 35, and an operation processing unit 36 as main elements. The image capturing unit 31, the communication I/F unit 32, the operation input unit 33, and the screen display unit 34 have the same functions as those of the image capturing unit 21, the communication I/F unit 22, the operation input unit 23, and the screen display unit 24 of the crack detection device 2 according to the second exemplary embodiment. Therefore, a description thereof will be omitted.

The storage unit 35 is a storage device such as a hard disk and a memory. The storage unit 35 has a function of storing processing information required for various types of processing in the operation processing unit 36 and a program 357. The program 357 is a program which is read and executed by the operation processing unit 36 to realize various processing units. The program 357 is read in advance from an external device (not illustrated) or a storage medium (not illustrated) via a data input/output function of the communication I/F unit 32 and the like, and is stored in the storage unit 35. Main information to be stored in the storage unit 35 includes image information 351, displacement distribution information 352, region information 353, crack-opening-displacement information 354, standard crack-opening-displacement information 355, and soundness information 356. The configurations of the image information 351, the displacement distribution information 352, and the region information 353 are similar to those of the image information 251, the displacement distribution information 252, and the region information 253 of the crack detection device 2 according to the second exemplary embodiment. Therefore, a description thereof will be omitted.

Figure 14:
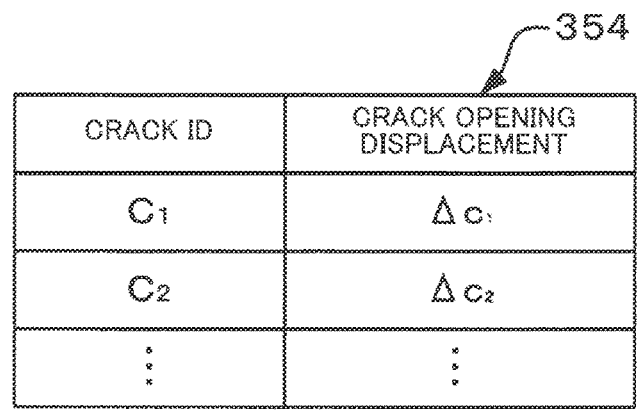
FIG. 14 is a diagram illustrating a configuration example of crack-opening-displacement information in the structure soundness evaluation device according to the third exemplary embodiment of the present invention.

The crack-opening-displacement information 354 is information which is calculated based on the displacement distribution information 352 and the region information 353 and indicates a displacement of a crack opening. FIG. 14 is a configuration example of the crack-opening-displacement information 354. Referring to FIG. 14, in the crack-opening-displacement information 354, a crack opening displacement indicating displacement of a crack opening is stored in association with a crack ID for identifying the crack 61. For example, the first row of FIG. 14 indicates that a displacement of the opening of the crack 61 of a crack ID "$C_1$" is "$\Delta_{C1}$". In addition, the crack-opening-displacement information 354 may include such information (a coordinate or a region ID of an adjacent region) as indicating the position in which the crack 61 exists. Furthermore, the crack-opening-displacement information 354 may include information indicating a time (for example, the time of acquisition of the image data used as a source) at which the crack width has been changed.

Figure 15:
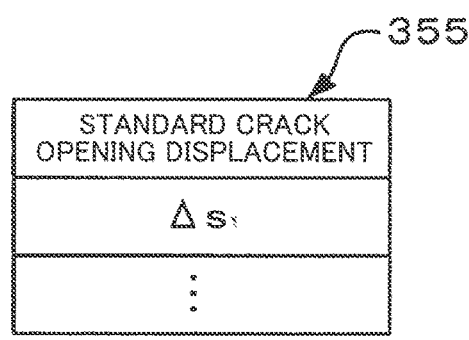
FIG. 15 is a diagram illustrating a configuration example of standard crack-opening-displacement information in the structure soundness evaluation device according to the third exemplary embodiment of the present invention.

The standard crack-opening-displacement information 355 is information indicating a standard crack opening displacement which is a displacement of a crack opening used as a standard when evaluating the soundness of the structure 6. The standard crack-opening-displacement information 355, for example, is inputted in advance via the communication I/F unit 32, the operation input unit 33 and the like, and is stored in the storage unit 35. FIG. 15 is a configuration example of the standard crack-opening-displacement information 355. Referring to FIG. 15, the standard crack-opening-displacement information 355 stores the standard crack opening displacement used as a standard when evaluating the soundness of the structure 6. For example, the first row of FIG. 15 indicates that the standard crack opening displacement is $\Delta_{s1}$. In addition, the standard crack-opening-displacement information 355 may include a plurality of standard crack opening displacements.

Figure 16:
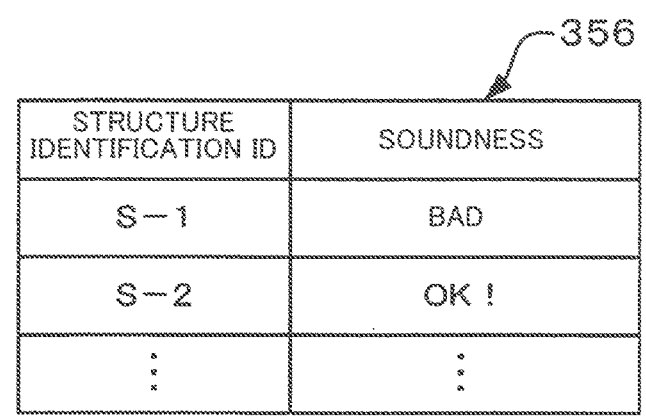
FIG. 16 is a diagram illustrating a configuration example of soundness information in the structure soundness evaluation device according to the third exemplary embodiment of the present invention.

The soundness information 356 is information which is calculated based on the crack opening displacement (see FIG. 14) and the standard crack opening displacement (see FIG. 15), and indicates the soundness of the structure 6. FIG. 16 is a configuration example of the soundness information 356. Referring to FIG. 16, in the soundness information 356, the soundness of the structure 6 is stored in association with the structure ID for identifying the structure 6. For example, the first row of FIG. 16 indicates that the soundness of the structure 6 with a structure ID of "S–1" is "bad". As will be described later, a kind of soundness included in the soundness information 356 corresponds to the value of the standard crack opening displacement included in the standard crack-opening-displacement information 355. Furthermore, the soundness illustrated in FIG. 16 is an example. The soundness, for example, may indicate the presence or absence of deterioration, the necessity of mend or repair, and the like.

The operation processing unit 36 has a microprocessor such as a MPU and a peripheral circuit thereof, and has a function of making the aforementioned hardware and the program 356 to cooperate with each other, and implementing various processing units, by reading the program 356 from the storage unit 35 to execute it. Main processing units implemented by the operation processing unit 36 include an image acquiring unit 361, a displacement feature calculating unit 362, a region division unit 363, a crack detection unit 364, a crack-opening-displacement calculating unit 365 (a crack-opening-displacement calculating means), a crack-opening-displacement comparing unit 366 (a first soundness evaluating means, a standard crack-opening-displacement comparing means), and a soundness output unit 367. The configurations of the image acquiring unit 361, the displacement feature calculating unit 362, and the region division unit 363 are similar to those of the image acquiring unit 261, the displacement feature calculating unit 262, and the region division unit 263 of the crack detection device 2 according to the second exemplary embodiment. Therefore, a description thereof will be omitted.

The crack detection unit 364 has a function of reading the region information 353 from the storage unit 35 and detecting the crack 61 based on the read region information 353. That is, the crack detection unit 364 has a function similar to that of the crack detection unit 264 of the crack detection device 2 according to the second exemplary embodiment. However, the crack detection unit 364 according to the present exemplary embodiment is configured to notify the crack-opening-displacement calculating unit 365 that the crack 61 is detected after detecting the crack 61.

The crack-opening-displacement calculating unit 365 has a function of reading the displacement distribution information 352 and the region information 353 from the storage unit 35 and calculating a displacement of the opening of the crack 61, which is detected by the crack detection unit 364, based on the read displacement distribution information 352 and region information 353.

For example, it is assumed that a crack 61 exists between the region α and the region β. In this case, when notified by the crack detection unit 364 of the detection of the crack 61, the crack-opening-displacement calculating unit 365 reads a corresponding displacement distribution from the displacement distribution information 352 of the storage unit 35 (for example, FIG. 8 (B)). Furthermore, from the region information 353 of the storage unit 35, the crack-opening-displacement calculating unit 365 reads information of two regions (that is, the region α and the region β) which across the boundary detected as the crack 61. Subsequently, based on the displacement distribution and the information on the region α and the region β, the crack-opening-displacement calculating unit 365 calculates displacement features of the region α and the region β. Then, based on the displacement features of the region α and the region β, the crack-opening-displacement calculating unit 365 calculates a displacement of the crack opening existing in the boundary between the region α and the region β. Concretely, for example, when it is assumed that displacement vectors of the region α and the region β are respectively [vector A] and [vector B], the crack-opening-displacement calculating unit 365 calculates a crack opening displacement based on the following formula.

$$[\text{vector } B] - [\text{vector } A]$$

Thereafter, the crack-opening-displacement calculating unit 365 associates the calculated crack opening displacement with information for identifying the crack 61 which is a calculation source of a crack opening displacement, and stores the result in the storage unit 35 as the crack-opening-displacement information 354.

In addition, the crack-opening-displacement calculating unit 365 may perform a vector operation including angle information between vectors, thereby calculating a crack opening displacement.

Furthermore, the crack-opening-displacement calculating unit 365 can calculate a displacement feature of region by using various methods. For example, the crack-opening-displacement calculating unit 365 may calculate the displacement feature of the region by calculating an average of displacement features in the region, or may use a displacement feature of a measurement point which is determined to be nearest to the boundary of each of the regions as the displacement feature of each of the regions. As described above, a method, by which the crack-opening-displacement calculating unit 365 calculate the displacement feature of each of the regions, is not particularly limited.

Furthermore, the crack-opening-displacement calculating unit 365 may be configured to calculate a crack opening displacement based on only the displacement distribution information 352 read from the storage unit 35.

The crack-opening-displacement comparing unit 366 has a function of reading the crack-opening-displacement information 354 and the standard crack-opening-displacement information 355 from the storage unit 35, and evaluating the soundness of the structure 6 based on the read crack-opening-displacement information 354 and the read standard crack-opening-displacement information 355. For example, the crack-opening-displacement comparing unit 366 reads "0.5 mm" as the crack opening displacement "$\Delta_{C1}$". Furthermore, the crack-opening-displacement comparing unit 366 reads "0.2 mm" as the standard crack opening displacement "$\Delta_{s1}$". Then, the crack-opening-displacement comparing unit 366 compares the crack opening displacement "$\Delta_{C1}$" with the standard crack opening displacement "$\Delta_{s1}$". In this case, the crack opening displacement "$\Delta_{C1}$" is larger than the standard crack opening displacement "$\Delta_{s1}$". Therefore, the crack-opening-displacement comparing unit 366 determines that the soundness of the structure 6 is bad for example.

Thereafter, the crack-opening-displacement comparing unit 366 associates the soundness, which is obtained by comparing the crack opening displacement with the standard crack opening displacement, with a structure identification ID for identifying the structure 6 (having the crack 61)

which is a target of the soundness, and stores the result in the storage unit 35 as the soundness information 356.

In addition, when a plurality of standard crack opening displacements are included in the standard crack-opening-displacement information 355, the crack-opening-displacement comparing unit 366 may be configured to evaluate the soundness on a scale by making comparison using respective standard crack opening displacements as threshold values.

The soundness output unit 367 has a function of reading the soundness information 356 from the storage unit 35 and displaying the soundness information 356 on the screen display unit 34. For example, the soundness output unit 367 also reads a corresponding displacement distribution from the displacement distribution information 352, thereby displaying the soundness superimposed on the displacement distribution on the screen display unit 34.

So far, the configuration of the structure soundness evaluation device 3 has been described.

Figure 17:
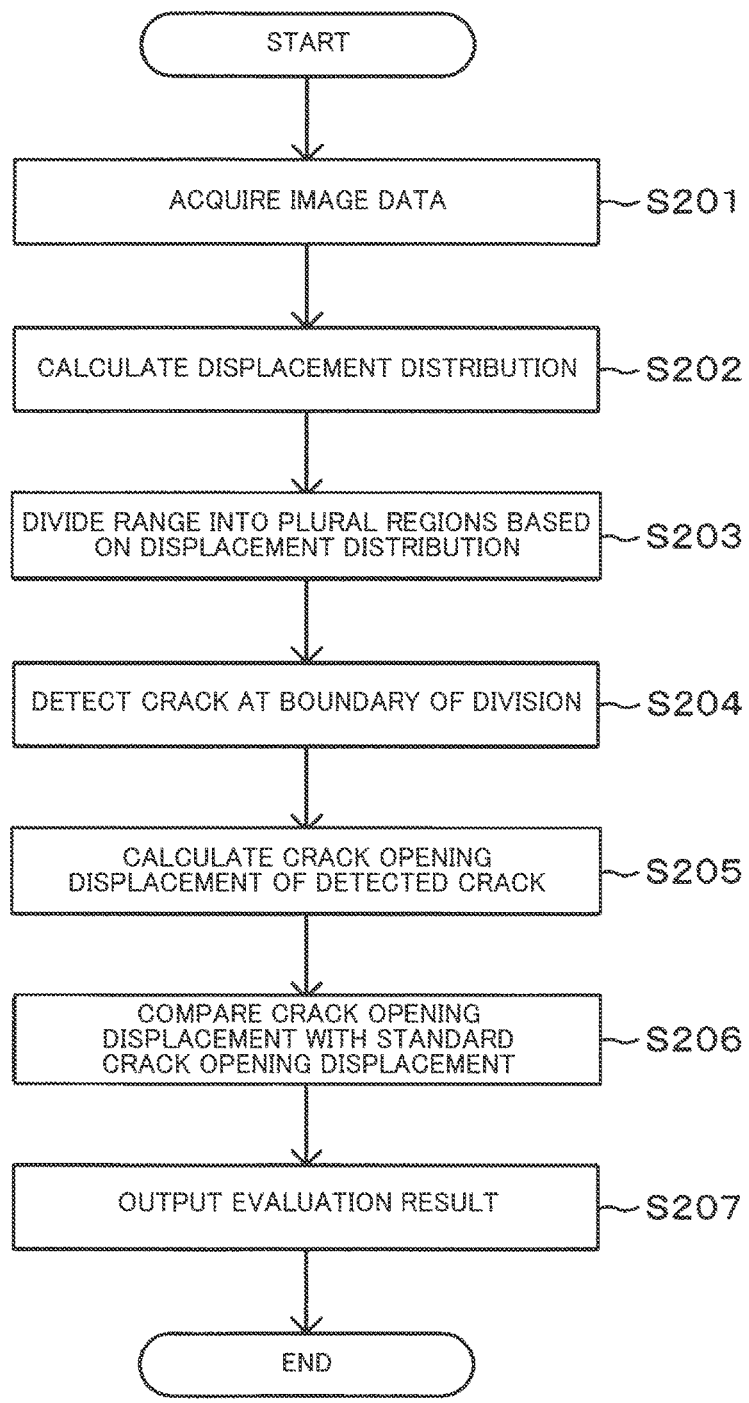
FIG. 17 is a flowchart for explaining an operation of the structure soundness evaluation device according to the third exemplary embodiment of the present invention.

Next, an operation of the structure soundness evaluation device 3 will be described. FIG. 17 is a flowchart illustrating the operation of the structure soundness evaluation device 3 according to the present exemplary embodiment. Hereinafter, with reference to FIG. 17, the operation of the structure soundness evaluation device 3 will be described. The operations of the structure soundness evaluation device 3 from step S201 to step S204 illustrated in FIG. 17 are completely the same as those from step S101 to step S104 of the crack detection device 2 according to the second exemplary embodiment (see FIG. 12). Therefore, hereinafter, the operation of the structure soundness evaluation device 3 after step S204 will be described.

As described above, by the operations similar to those of the crack detection device 2 according to the second exemplary embodiment, the crack detection unit 364 of the structure soundness evaluation device 3 detects the crack 61 (step S204). Then, the crack detection unit 364 notifies the crack-opening-displacement calculating unit 365 of the fact that the crack 61 is detected.

Next, the crack-opening-displacement calculating unit 365 calculates a crack opening displacement based on the displacement distribution stored in the displacement distribution information 352 of the storage unit 35 and the information on the two regions, which are stored in the region information 353, across the boundary which is determined as the crack 61 (step S205). Concretely, based on the aforementioned information, the crack-opening-displacement calculating unit 365 respectively calculates displacement features of the two regions across the boundary which is determined the crack 61. Then, based on the displacement features of the regions across the crack 61, the crack-opening-displacement calculating unit 365 calculates the crack opening displacement. Thereafter, the crack-opening-displacement calculating unit 365 stores the calculated crack opening displacement in the crack-opening-displacement information 354.

Subsequently, the crack-opening-displacement comparing unit 366 compares the crack opening displacement stored in the crack-opening-displacement information 354 of the storage unit 35 with the standard crack opening displacement stored in the standard crack-opening-displacement information 355 (step S206), and evaluates the soundness of the structure 6. Then, the crack-opening-displacement comparing unit 366 stores the evaluation result in the soundness information 356.

Thereafter, the soundness output unit 367 reads the soundness information 356 of the storage unit 35 and displays the read soundness information 356 on the screen display unit 34 (step S207).

As described above, the structure soundness evaluation device 3 according to the present exemplary embodiment has the crack-opening-displacement calculating unit 365 and the crack-opening-displacement comparing unit 366. Furthermore, the structure soundness evaluation device 3 stores the standard crack opening displacement. By such a configuration, the crack-opening-displacement comparing unit 366 can compare the crack opening displacement calculated by the crack-opening-displacement calculating unit 365 with the standard crack opening displacement, thereby evaluating the soundness of the structure 6. As described above, the structure soundness evaluation device 3 according to the present exemplary embodiment can detect the crack 61 formed on the surface of the structure 6 without erroneously detecting a pattern or the like similar in appearance on an image to the crack 61. Therefore, by evaluating the soundness of the structure 6 based on the displacement of the crack opening of the detected crack 61, it is possible to more accurately evaluate the soundness of the structure 6.

In general, when the crack 61 is detected by using an image, it is difficult to accurately detect the width of a minute crack 61 equal to or less than 1 pixel. Therefore, it may seem difficult to accurately calculate soundness calculated as the result. However, even though it is difficult to accurately detect the width of a minute crack 61, when applying a region-based image search method typified by a template matching method or a digital image correlation method, it is easy to calculate a displacement of the opening of the crack 61 with sub-pixel accuracy of equal to or less than 1 pixel in many cases. Therefore, by calculating soundness of the structure 6 based on the displacement of the opening of the crack 61, it is possible to obtain the soundness more accurately and more easily.

As described above, the width of the crack 61 is changed by various influences. Therefore, it is difficult for the structure soundness evaluation device 3 to perform constant soundness evaluation. However, for example, when the size of external force applied to the structure 6 is known, that is, when a truck and the like with a known weight is traveled on the structure 6, the structure soundness evaluation device 3 can accurately evaluate the soundness of the structure 6. Furthermore, for example, even when the size of the external force applied to the structure 6 is not known, for example, by utilizing the present invention to each of image data acquired in time series, it is possible to evaluate the state of the structure 6 in the worst case (when the crack width is maximal). In this regard, the structure soundness evaluation device 3 is considered to be useful in search (screening) and the like of abnormal places.

Furthermore, by utilizing the present invention to each of the time-series image data, the structure soundness evaluation device 3 can perform comparison with the standard crack opening displacement, while adding information on a speed, an acceleration and the like. As a consequence, it is possible to more finely evaluate the soundness of the structure 6, the seriousness of the crack 61, and the like.

Furthermore, it is assumed that the structure soundness evaluation device 3 according to the present exemplary embodiment has a configuration similar to that of the crack detection device 2 according to the second exemplary embodiment. However, the structure soundness evaluation device 3 may be configured to evaluate the soundness of the structure 6 based on the detection result of the crack 61 by the crack detection device 1 according to the first exemplary embodiment. That is, the structure soundness evaluation device 3 can be configured to calculate a crack opening displacement with respect to the crack 61 detected by the crack detection device 1, and to evaluate the soundness of the structure 6 based on the calculated crack opening displacement.

Furthermore, the structure soundness evaluation device 3 can be configured to calculate a displacement distribution between image data acquired in time series to detect the cracks 61, and to calculate crack opening displacements between the detected cracks 61. In this case, the structure soundness evaluation device 3 can be configured to compare the maximal crack opening displacement among the respectively calculated crack opening displacement with the standard crack opening displacement, and to evaluate soundness. With this configuration, as described above, it is possible to evaluate the state of the structure 6 in the worst case (when the crack width is maximal).

Figure 18:
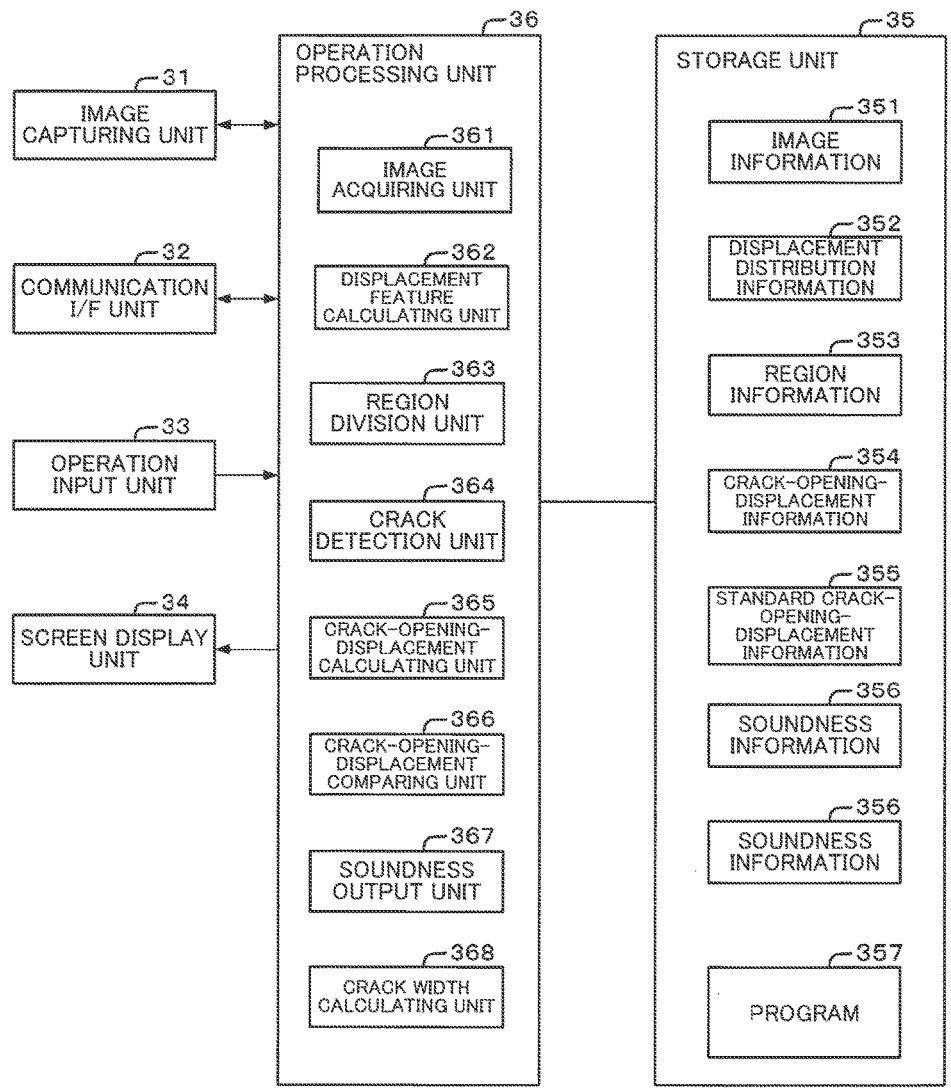
FIG. 18 is a block diagram illustrating another configuration example of the structure soundness evaluation device according to the third exemplary embodiment of the present invention.

Furthermore, when the crack opening displacements are calculated in time series as described above, the structure soundness evaluation device 3 can determine a maximal value of the crack opening displacements. As describe above, when the crack opening displacement is maximal, it follows that the crack width is widening. Therefore, it is assumed that the crack width itself is easier to measure than when the crack width is not changed. In this regard, the structure soundness evaluation device 3 can be configured to measure a crack width when the crack opening displacement is maximal, by using image data in which a crack opening displacement is maximal, and to evaluate the soundness of the structure 6 based on the measured crack width. For example, as illustrated in FIG. 18, the structure soundness evaluation device 3 can be configured to include a crack width calculating unit 368 (a crack width calculating means) that calculates a crack width based on image data when the crack opening displacement is maximal. Furthermore, the structure soundness evaluation device 3 can be configured to evaluate the soundness of a structure based on a calculation result by the crack width calculating unit 368. In addition, the calculation of a crack width by the crack width calculating unit 368 can use, for example, a known method such as measurement of the number of pixels between both sides of a crack (portions at which a luminance value differs). Furthermore, for example, the crack width calculating unit 368 of the structure soundness evaluation device 3 may be configured to arrange a calibration bar on the surface of the structure 6 to calculate a density value histogram, and to calculate a crack width from the measured density value.

Next, a fourth exemplary embodiment of the present invention will be described in detail with reference to the drawings.

Fourth Exemplary Embodiment

In the fourth exemplary embodiment, a description will be provided for a structure soundness evaluation device 4 including a means for acquiring external force (stress being generated) applied to the structure 6. As will be described later, the structure soundness evaluation device 4 is configured to calculate a crack opening displacement at standard external force, based on a calculated crack opening displacement and the external force applied to the structure 6 at the time of the calculation of the crack opening displacement. The structure soundness evaluation device 4 according to the present exemplary embodiment compares the crack opening displacement at standard external force with a standard crack opening displacement, thereby evaluating the soundness of the structure 6. In the present exemplary embodiment, a description will be provided for the case in which image data is acquired in time series and a crack opening displacement is calculated in time series based on the image data acquired in time series. Furthermore, in the present exemplary embodiment, the time of a change in a crack width is configured to be referable.

Figure 19:
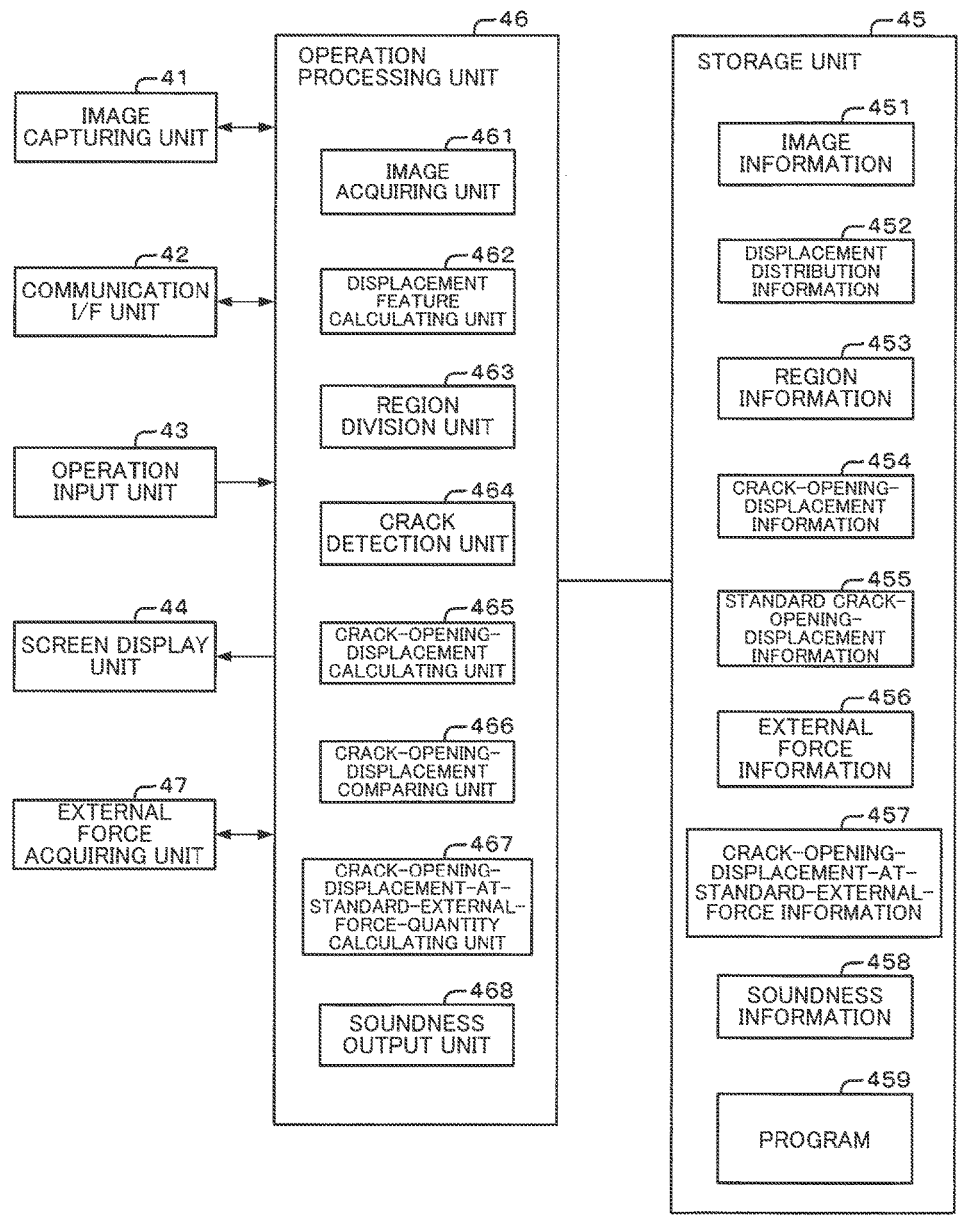
FIG. 19 is a block diagram illustrating a configuration of a structure soundness evaluation device according to a fourth exemplary embodiment of the present invention.

Referring to FIG. 19, the structure soundness evaluation device 4 according to the present exemplary embodiment has an image capturing unit 41, a communication I/F unit 42, an operation input unit 43, a screen display unit 44, a storage unit 45, an operation processing unit 46, and an external force acquiring unit 47 (an external force acquiring means) as main elements. The image capturing unit 41, the communication I/F unit 42, the operation input unit 43, and the screen display unit 44 have the same functions as those of the image capturing unit 31, the communication I/F unit 32, the operation input unit 33, and the screen display unit 34 of the structure soundness evaluation device 3 according to the third exemplary embodiment. Therefore, a description thereof will be omitted.

The storage unit 45 is a storage device such as a hard disk and a memory. The storage unit 45 has a function of storing processing information required for various types of processing in the operation processing unit 46 and a program 459. The program 459 is a program which is read and executed by the operation processing unit 46 to realize various processing units. The program 459 is read in advance from an external device (not illustrated) or a storage medium (not illustrated) via a data input/output function of the communication I/F unit 42 and the like, and is stored in the storage unit 45. Main information to be stored in the storage unit 45 includes image information 451, displacement distribution information 452, region information 453, crack-opening-displacement information 454, standard crack-opening-displacement information 455, external force information 456, crack-opening-displacement-at-standard-external-force information 457, and soundness information 458. The configurations of the image information 451, the displacement distribution information 452, the region information 453, the crack-opening-displacement information 454, the standard crack-opening-displacement information 455, and the soundness information 458 are similar to those of the image information 351, the displacement distribution information 352, the region information 353, the crack-opening-displacement information 354, the standard crack-opening-displacement information 355, and the soundness information 356 of the structure soundness evaluation device 3 according to the third exemplary embodiment. Therefore, a description thereof will be omitted.

Figure 20:
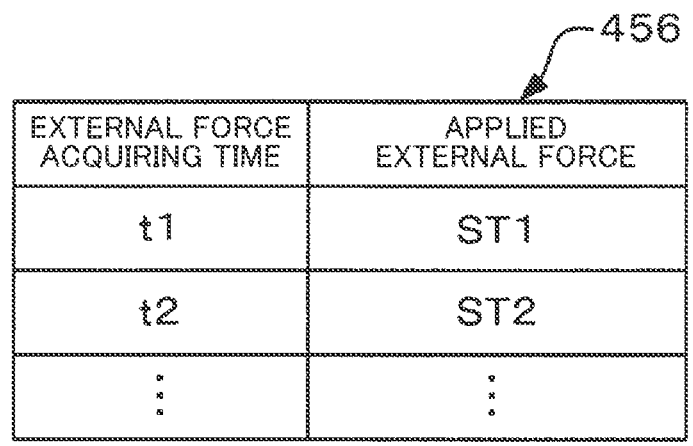
FIG. 20 is a diagram illustrating a configuration example of external force information in the structure soundness evaluation device according to the fourth exemplary embodiment of the present invention.

The external force information 456 is information acquired by the external force acquiring unit 47 and indicating the size of external force applied to the structure 6. As will be described later, the external force acquiring unit 47 is configured to acquire the external force, which is applied to the structure 6, at each time decided in advance. Therefore, the external force information 456 stores external force in time series. FIG. 20 is a configuration example of the external force information 456. Referring to FIG. 20, in the external force information 456, applied external force, which is external force applied to the structure 6, is stored in association with external force acquiring times which are times when external force is acquired. For example, the first row of FIG. 20 indicates that external force "ST1" has been applied to the structure 6 at a time "t1". In addition, the external force information 456 may be information indicating a magnitude of stress calculated based on external force.

Figure 21:
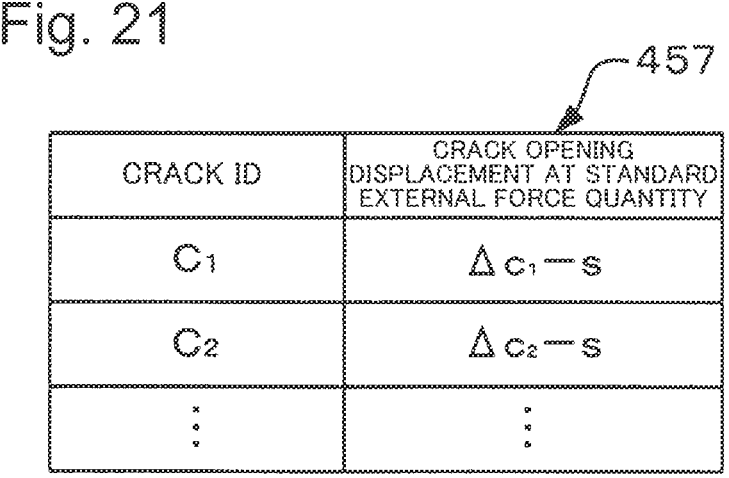
FIG. 21 is a diagram illustrating a configuration example of information of crack opening displacement caused by applying standard-external-force in the structure soundness evaluation device according to the fourth exemplary embodiment of the present invention.

The crack-opening-displacement-at-standard-external-force information 457 is information calculated based on the crack-opening-displacement information 454 and the external force information 456 and indicating a crack opening displacement at standard external force. FIG. 21 is a configuration example of the crack-opening-displacement-at-standard-external-force information 457. Referring to FIG. 21, the crack-opening-displacement-at-standard-external-force information 457 stores the crack opening displacement at standard external force, which is a crack opening displacement at a time when the standard external force is applied, in association with a crack ID for identifying the crack 61. For example, the first row of FIG. 21 indicates that, when standard external force is applied, a crack opening displacement of the crack 61 with a crack ID "$C_1$" is "$\Delta_{C1}$-s". The crack-opening-displacement-at-standard-external-force information 457 may be information indicating a crack opening displacement at the time of the generation of standard stress.

The operation processing unit 46 has a microprocessor such as a MPU and a peripheral circuit thereof, and has a function of making the aforementioned hardware and the program 459 cooperate with each other, and implementing various processing units, by reading the program 459 from the storage unit 45 to execute it. Main processing units implemented by the operation processing unit 46 include an image acquiring unit 461, a displacement feature calculating unit 462, a region division unit 463, a crack detection unit 464, a crack-opening-displacement calculating unit 465, a crack-opening-displacement comparing unit 466, a crack-opening-displacement-at-standard-external-force calculating unit 467 (crack-opening-displacement-at-standard-external-force estimating means), and a soundness output unit 468. The configurations of the image acquiring unit 461, the displacement feature calculating unit 462, the region division unit 463, the crack detection unit 464, the crack-opening-displacement calculating unit 465, and the soundness output unit 468 are similar to those of the image acquiring unit 361, the displacement feature calculating unit 362, the region division unit 363, the crack detection unit 364, the crack-opening-displacement calculating unit 365, and the soundness output unit 367 of the structure soundness evaluation device 3 according to the third exemplary embodiment. Therefore, a description thereof will be omitted.

The crack-opening-displacement comparing unit 466 has a function of evaluating the soundness of the structure 6 based on the crack-opening-displacement-at-standard-external-force information 457 and the standard crack-opening-displacement information 455 read from the storage unit 45. That is, the crack-opening-displacement comparing unit 466 is different from the crack-opening-displacement comparing unit 366 of the structure soundness evaluation device 3 according to the third exemplary embodiment in the point of comparing by using the crack-opening-displacement-at-standard-external-force information 457 instead of the crack-opening-displacement information 454. The other configurations of the crack-opening-displacement comparing unit 465, except for the aforementioned configuration, are similar to those of the crack-opening-displacement comparing unit 366.

The crack-opening-displacement-at-standard-external-force calculating unit 467 has a function of calculating a crack opening displacement when standard external force has been applied to the structure 6, based on the crack-opening-displacement information 454 and the external force information 456, which are read from the storage unit 45.

For example, the crack-opening-displacement-at-standard-external-force calculating unit 467 reads the crack opening displacement "$\Delta_{C1}$" of the crack ID "$C_1$" from the crack-opening-displacement information 454 of the storage unit 45. Furthermore, the crack-opening-displacement-at-standard-external-force calculating unit 467 reads a time when the crack width is changed, from the crack-opening-displacement information 454 of the storage unit 45. Moreover, the crack-opening-displacement-at-standard-external-force calculating unit 467 reads applied external force applied to the structure 6 at the time when the crack width is changed, from the external force information 456 of the storage unit 45. For example, the crack-opening-displacement-at-standard-external-force calculating unit 467 reads the applied external force "ST1" at the time of "t1" when the crack width is changed.

The crack-opening-displacement-at-standard-external-force calculating unit 467 respectively performs the reading of the aforementioned information to the crack-opening-displacement information 454 of time-series. Then, the crack-opening-displacement-at-standard-external-force calculating unit 467 calculates, by using the read information respectively, the inclination of the crack opening displacement at the time of the applied external force increase, and calculates a crack opening displacement in the case of the standard external force being applied.

Figure 22:
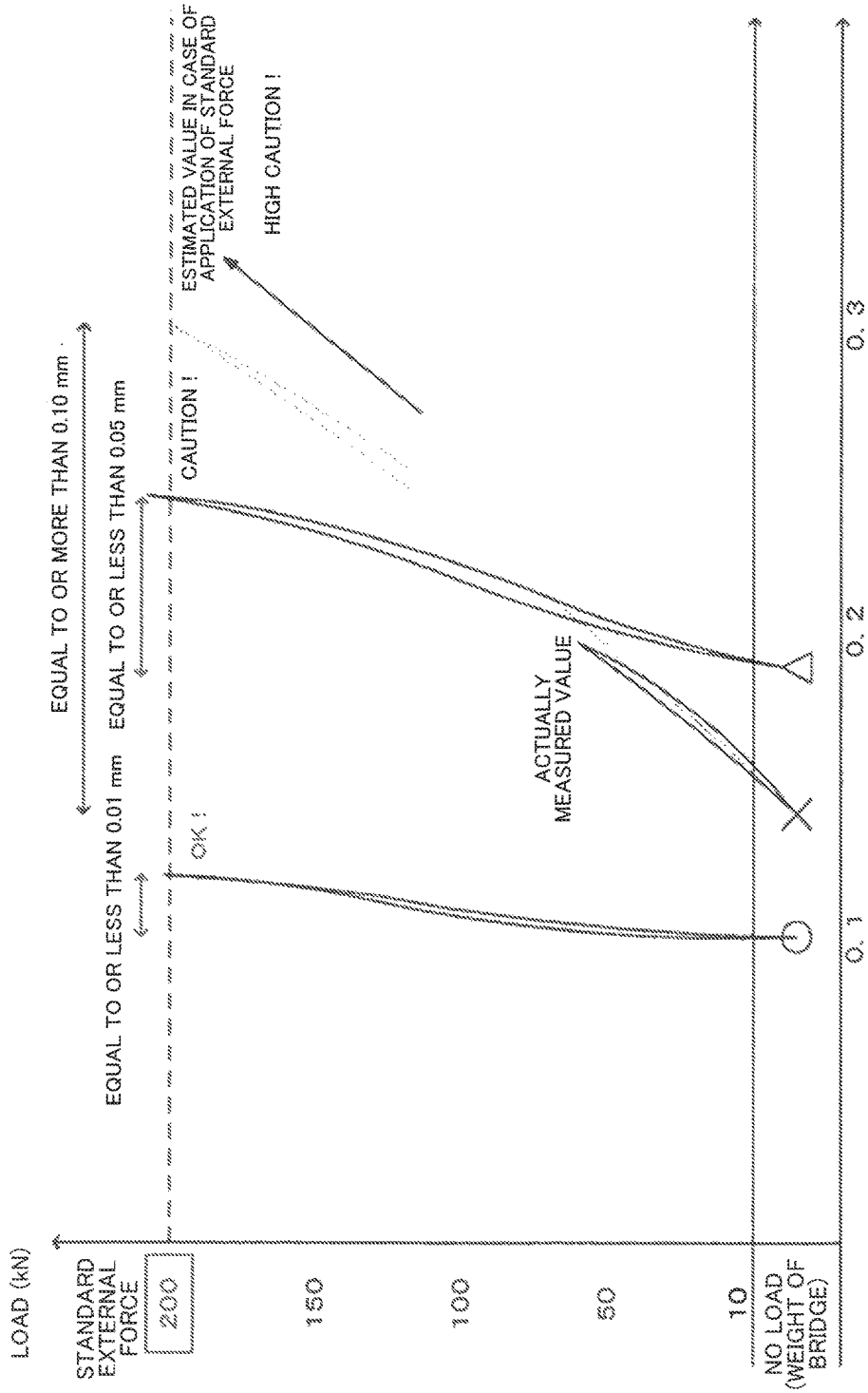
FIG. 22 is a diagram illustrating an example of calculation of information of crack opening displacement caused by applying standard-external-force in the structure soundness evaluation device according to the fourth exemplary embodiment of the present invention.

Concretely, a case with a standard external force of 200 kN will be described. In this case, for example, it is assumed that a crack opening displacement is obtained only at an applied external force of around 50 kN as an actually measured value. Even in this case, referring to FIG. 22, the crack-opening-displacement-at-standard-external-force calculating unit 467 can calculate the inclination of the crack opening displacement at the applied external force around 50 kN, thereby calculating a crack opening displacement at a time when the standard external force of 200 kN is applied.

Thereafter, the crack-opening-displacement-at-standard-external-force calculating unit 467 stores the calculated result in the storage unit 45 as the crack-opening-displacement-at-standard-external-force information 457. That is, the crack-opening-displacement-at-standard-external-force calculating unit 467 associates the crack ID with the crack-opening-displacement-at-standard-external-force, and stores the result in the storage unit 45 as the crack-opening-displacement-at-standard-external-force information 457.

The external force acquiring unit 47 has a function of acquiring external force applied to the structure 6 at each of predetermined time. The external force acquiring unit 47, for example, measures a weight of a vehicle travelling on the structure 6, thereby acquiring external force applied to the structure 6. In addition, the external force acquiring unit 47 may acquire external force applied to the structure 6 in consideration of an acceleration of the structure 6 itself when vibration of earthquake, stroke and the like is applied. Furthermore, the external force acquiring unit 47 may be configured to acquire applied external force from a deformation amount such as deflection occurred at a time of external force being applied to the structure 6. Furthermore, the external force acquiring unit 47 may be configured to acquire stress generated on the structure 6, based on the acquired external force.

Concretely, the external force acquiring unit 47, for example, includes a vehicle model estimation sensor. By specifying the model of a vehicle travelling on the structure 6 using the vehicle model estimation sensor, the external force acquiring unit 47 acquires external force applied to the structure 6. Thereafter, the external force acquiring unit 47 stores the acquired external force in the external force information 456 in association with the time of the external force acquisition.

So far, the configuration of the structure soundness evaluation device 4 has been described.

Figure 23:
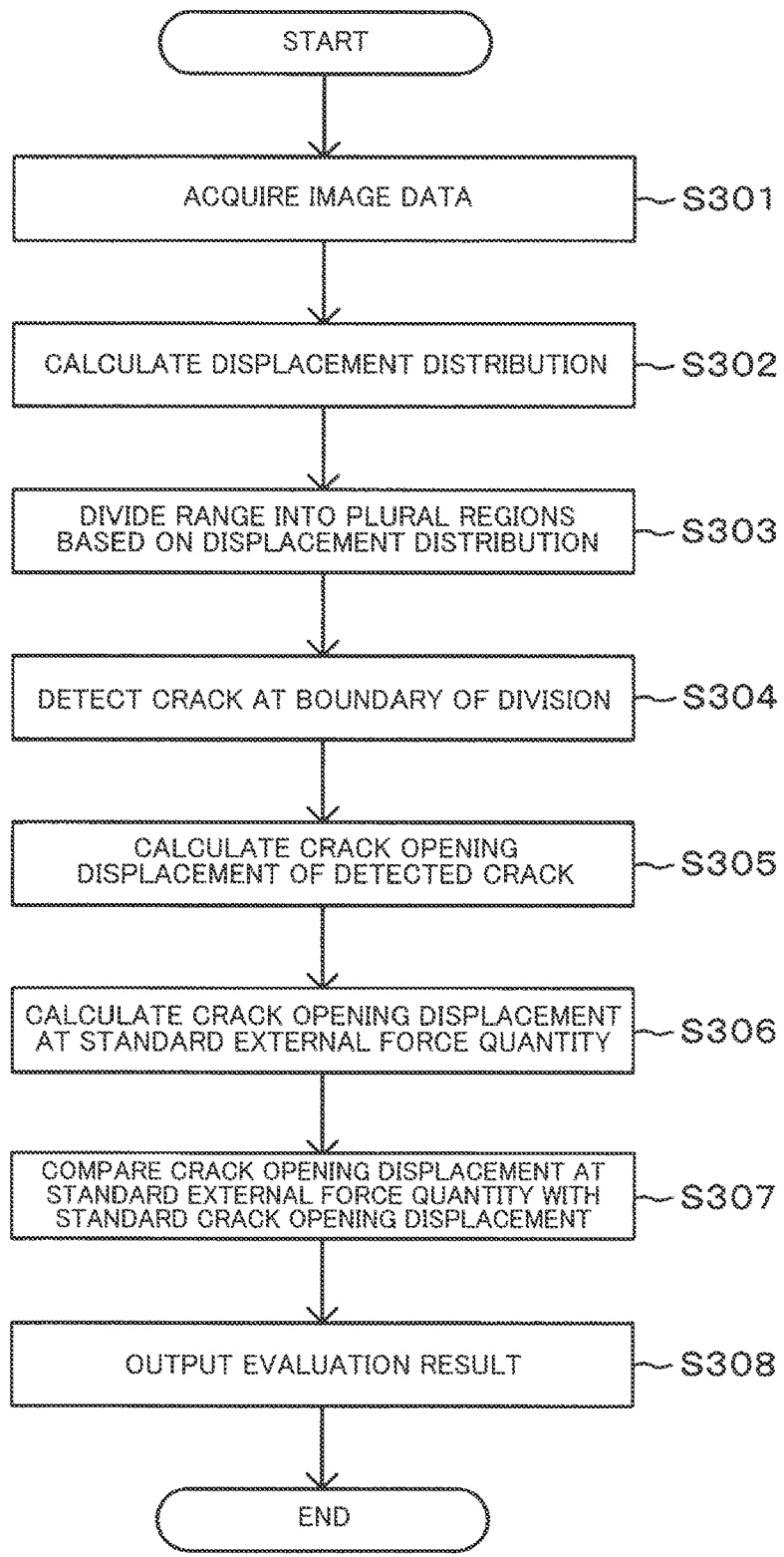
FIG. 23 is a flowchart for explaining an operation of the structure soundness evaluation device according to the fourth exemplary embodiment of the present invention.

Next, an operation of the structure soundness evaluation device 4 will be described. FIG. 23 is a flowchart illustrating the operation of the structure soundness evaluation device 4 according to the present exemplary embodiment. Hereinafter, with reference to FIG. 23, the operation of the structure soundness evaluation device 4 will be described. The operations of the structure soundness evaluation device 4 from step S301 to step S305 illustrated in FIG. 23 are completely the same as those from step S201 to step S205 of the crack detection device 3 according to the third exemplary embodiment (see FIG. 17). Therefore, hereinafter, the operation of the structure soundness evaluation device 4 after step S306 will be described.

As described above, by the operations similar to those of the structure soundness evaluation device 3 according to the third exemplary embodiment, the crack-opening-displacement calculating unit 465 of the structure soundness evaluation device 4 calculates a crack opening displacement (step S305). Then, the crack-opening-displacement calculating unit 465 stores the calculated crack opening displacement in the crack-opening-displacement information 454.

Furthermore, the external force acquiring unit 47 acquires external force being applied to the structure 6 at each of predetermined time. Then, the external force acquiring unit 47 associates the acquired external force with the time of the external force acquisition and stores the result in the external force information 456.

Next, the crack-opening-displacement-at-standard-external-force calculating unit 467 calculates a crack opening displacement at standard external force, based on the crack opening displacement stored in the crack-opening-displacement information 454 of the storage unit 45 and the applied external force stored in the external force information 456 (step S306). Then, the crack-opening-displacement-at-standard-external-force calculating unit 467 stores the calculated crack opening displacement at standard external force in the crack-opening-displacement-at-standard-external-force information 457 of the storage unit 45.

Subsequently, the crack-opening-displacement comparing unit 466 compares the calculated crack opening displacement at standard external force stored in the crack-opening-displacement-at-standard-external-force information 457 of the storage unit 45 with the standard crack opening displacement stored in the standard crack-opening-displacement information 455 (step S307), and evaluates the soundness of the structure 6. Then, the crack-opening-displacement comparing unit 466 stores the evaluation result in the soundness information 458.

Thereafter, the soundness output unit 468 reads the soundness information 458 of the storage unit 45 and displays the read soundness information 458 on the screen display unit 44 (step S308).

As described above, the structure soundness evaluation device 4 according to the present exemplary embodiment has the crack-opening-displacement-at-standard-external-force calculating unit 467. By such a configuration, the crack-opening-displacement comparing unit 466 of the structure soundness evaluation device 4 can evaluate soundness as a result of comparing the crack opening displacement at standard external force, which is calculated by the crack-opening-displacement-at-standard-external-force calculating unit 467, with the standard crack opening displacement. As a consequence, the structure soundness evaluation device 4 can perform constant soundness evaluation.

In addition, the structure soundness evaluation device 4 may be configured to perform comparison with the standard crack opening displacement, in consideration of information such as a speed, an acceleration and the like of the structure itself by applied external force.

Furthermore, the structure soundness evaluation device 4 may be configured to evaluate the soundness of the structure 6 based on the detection result of the crack 61 by the crack detection device 1 according to the first exemplary embodiment. That is, the structure soundness evaluation device 4 can be configured to calculate a crack opening displacement with respect to the crack 61 detected by the crack detection device 1, and calculate a crack opening displacement at standard external force, based on the calculated crack opening displacement.

Furthermore, the structure soundness evaluation device 4 can be configured to measure a crack width when a crack opening displacement is maximal and evaluate the soundness of the structure 6 based on the measured crack width. The measurement of the crack width is performed by using, for example, a known method such as measurement of the number of pixels between both sides of a crack (portions at which a luminance value differs). Furthermore, for example, the structure soundness evaluation device 3 may be configured to arrange a calibration bar on the surface of the structure 6 to calculate a density value histogram, and to calculate a crack width from the measured density value.

Next, a fifth exemplary embodiment of the present invention will be described in detail with reference to the drawings.

Fifth Exemplary Embodiment

In the fifth exemplary embodiment, a description will be provided for a crack depth evaluation device 7 that calculates the displacement of the opening of the crack 61 and evaluates the depth of the crack 61 formed on the surface of the structure 6, based on the calculated displacement of the opening of the crack 61 and external force applied to the structure 6 from an exterior.

Figure 24:
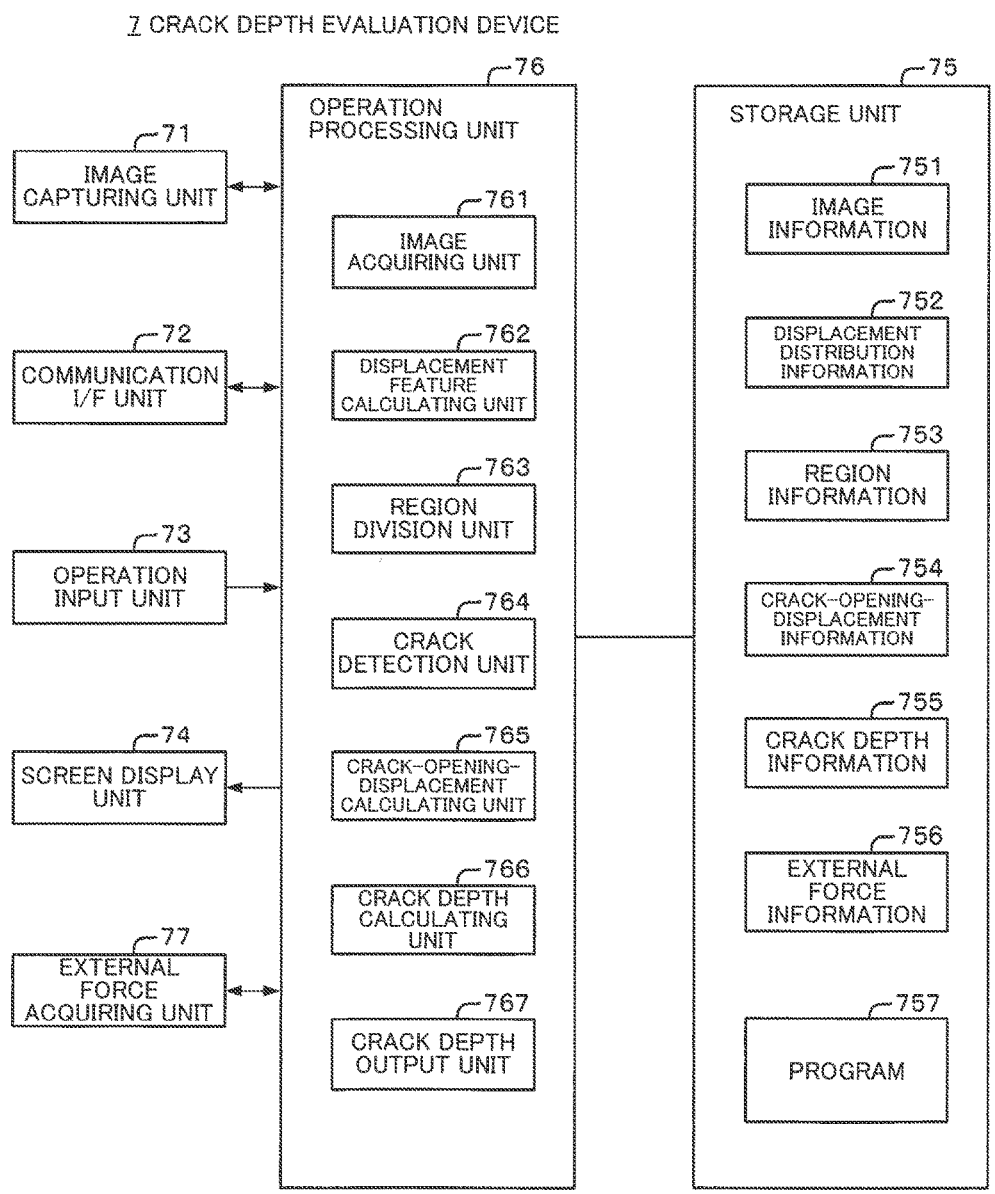
FIG. 24 is a block diagram illustrating a configuration of a crack depth evaluation device according to a fifth exemplary embodiment of the present invention.

Referring to FIG. 24, the crack depth evaluation device 7 according to the present exemplary embodiment has an image capturing unit 71, a communication I/F unit 72, an operation input unit 73, a screen display unit 74, a storage unit 75, an operation processing unit 76, and an external force acquiring unit 77 as main elements. The image capturing unit 71, the communication I/F unit 72, the operation input unit 73, and the screen display unit 74 have the same functions as those of the image capturing unit 21, the communication I/F unit 22, the operation input unit 23, and the screen display unit 24 of the crack detection device 2 according to the second exemplary embodiment. Furthermore, the external force acquiring unit 77 has the same functions as those of the external force acquiring unit 47 of the structure soundness evaluation device 4 according to the fourth exemplary embodiment. Therefore, a description thereof will be omitted.

The storage unit 75 is a storage device such as a hard disk and a memory. The storage unit 75 has a function of storing processing information required for various types of processing in the operation processing unit 76 and a program 757. The program 757 is a program which is read and executed by the operation processing unit 76 to realize various processing units. The program 757 is read in advance from an external device (not illustrated) or a storage medium (not illustrated) via a data input/output function of the communication I/F unit 72 and the like, and is stored in the storage unit 75. Main information to be stored in the storage unit 75 includes image information 751, displacement distribution information 752, region information 753, crack-opening-displacement information 754, crack depth information 755, and external force information 756. The configurations of the image information 751, the displacement distribution information 752, and the region information 753 are similar to those of the image information 251, the displacement distribution information 252, and the region information 253 of the crack detection device 2 according to the second exemplary embodiment. Furthermore, the configuration of the crack-opening-displacement information 754 is similar to that of the crack-opening-displacement information 354 of the structure soundness evaluation device 3 according to the third exemplary embodiment. Furthermore, the configuration of the external force information 756 is similar to that of the external force information 456 of the structure soundness evaluation device 4 according to the fourth exemplary embodiment. Therefore, a description thereof will be omitted.

Figure 25:
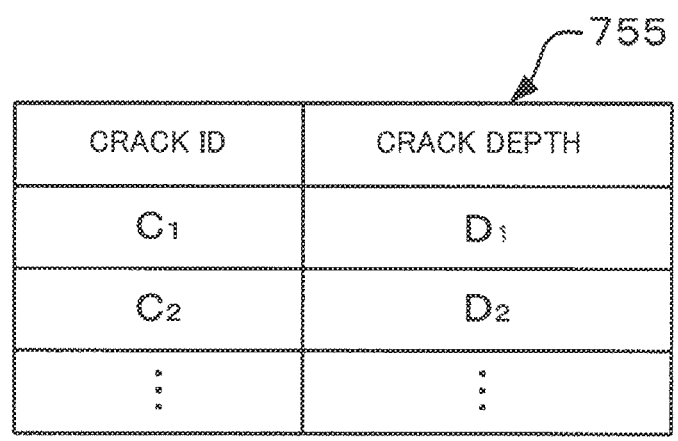
FIG. 25 is a diagram illustrating a configuration example of crack depth information in the crack depth evaluation device according to the fifth exemplary embodiment of the present invention.

The crack depth information 755 is information calculated based on the crack-opening-displacement information 754 and the external force information 756 and indicating the depth of a crack. FIG. 25 is a configuration example of the crack depth information 755. Referring to FIG. 25, in the crack depth information 755, a crack ID for identifying the crack 61 and a crack depth indicating the depth of a crack are stored in association with each other. For example, the first row of FIG. 25 indicates that a crack depth with a crack ID "$C_1$" is "$D_1$".

The crack depth information 755 may include information (for example, a coordinate and a region ID of an adjacent region) indicating the position in which the crack 61 exists. Furthermore, the crack depth information 755 may include information indicating a time of measurement of the depth of the crack (for example, the time of acquisition of the image data used as a source).

The operation processing unit 76 has a microprocessor such as an MPU and a peripheral circuit thereof, and has a function of making the aforementioned hardware and the program 757 cooperate with each other, and implementing various processing units, by reading the program 757 from the storage unit 75 to execute it. Main processing units implemented by the operation processing unit 76 include an image acquiring unit 761, a displacement feature calculating unit 762, a region division unit 763, a crack detection unit 764, a crack-opening-displacement calculating unit 765, a crack depth calculating unit 766 (a crack depth calculating means), and a crack depth output unit 767. The configurations of the image acquiring unit 761, the displacement feature calculating unit 762, and the region division unit 763 are similar to those of the image acquiring unit 261, the displacement feature calculating unit 262, and the region division unit 263 of the crack detection device 2 according to the second exemplary embodiment. Furthermore, the configurations of the crack detection unit 764 and the crack-opening-displacement calculating unit 765 are similar to those of the crack detection unit 364 and the crack-opening-displacement calculating unit 365 of the structure soundness evaluation device 3 according to the third exemplary embodiment. Therefore, a description thereof will be omitted.

The crack depth calculating unit 766 reads the crack-opening-displacement information 754 and the external force information 756 from the storage unit 75, and calculates the crack depth of the crack 61 based on the read crack-opening-displacement information 754 and the read external force information 756. Then, the crack depth calculating unit 766 associates the calculated crack depth with information for identifying the crack 61 and stores the result in the storage unit 75 as the crack depth information 755.

Concretely, for example, description will be given to a case of evaluating the crack depth $D_1$ of the crack 61 formed on the surface of the structure 6 when external force F is applied to the structure 6. In this case, when it is assumed that a crack opening displacement is $\Delta C_1$, the following relation is considered to exist among the external force F, the crack depth $D_1$, and the crack opening displacement $\Delta C_1$.

(crack opening displacement $\Delta C_1$)=(external force $F$)×(constant $a$)×(crack depth $D_1$)

The constant a is a constant depending on the material and structure of the structure 6.

From the above relation, the crack depth $D_1$ is obtained by the following Equation.

(crack depth $D_1$)=(crack opening displacement $\Delta C_1$)/ ((external force $F$)×(constant $a$))

The above Equation holds as far as the external force is applied within a range that allows a linear elastic deformation in the structure.

The crack depth calculating unit 766, for example, calculates the crack depth $D_1$ from the crack opening displacement $\Delta C_1$ indicated by the crack-opening-displacement information 754 and the external force F indicated by the external force information 756 by using the aforementioned Equation. Then, the crack depth calculating unit 766 associates the calculated crack depth $D_1$ with information for identifying the crack 61 which is a calculation source of the crack width depth displacement, and stores the result in the storage unit 75 as the crack depth information 755.

In addition, the crack depth calculating unit 766 can calculate the crack depth $D_1$ by using a crack opening displacement $\Delta C$, which is calculated by using various methods, and external force F.

For example, the crack depth calculating unit 766 can calculate the crack depth $D_1$ by using external force F, when a vehicle with a known weight is loaded as a static load, and a crack opening displacement $\Delta C$ observed at this time. Furthermore, the crack depth calculating unit 766 may calculate the crack depth $D_1$ by using external force F, when a vehicle is traveled as a dynamic load, and a crack opening displacement $\Delta C$ at this time. Furthermore, when external force is applied by a weight moving up and down at a constant cycle and is repeatedly changed, the crack depth calculating unit 766 may calculate the crack depth $D_1$ by using a relation between a crack opening displacement $\Delta C$ being changed and external force F at this time.

Furthermore, the constant a, which depends on a material and a structure and is used when the crack depth calculating unit 766 calculates the crack depth $D_1$, can be calculated by using various methods.

For example, the constant depending on a material and a structure can be calculated in advance by using a known crack. For example, a crack opening displacement $\Delta C$ is acquired when a certain load (external force) F is applied to the structure 6, and an actual measured value of the crack depth D is acquired in advance by using actual measurement by needle insertion for depth measurement or a result of actual crack depth measurement using a ultrasonic method or an impact elastic wave. Then, the constant a, which depends on a material and a structure, can be calculated in advance based on a relational equality of crack depth $D=\Delta C/(F \times a)$ by using the above information. As described above, the crack depth calculating unit 766 can use the constant a, which depends on a material and a structure and is calculated in advance, when calculating the crack depth $D_1$. Furthermore, the crack depth calculating unit 766, for example, may be configured to calculate the constant a, which depends on a material and a structure, by calculation from a deformation amount such as deflection occurred at a time of external force being applied to the structure 6, based on material information and structure information.

In addition, when performing relative evaluation of crack depths D occurring in structures with the same material and structure, the constant a depending on a material and a structure can be treated as a constant as is. In such a case, by comparing coefficients of the constant a, it is possible to perform the relative evaluation of the crack depth D among the structures with the same material and structure.

The crack depth output unit 767 has a function of reading the crack depth information 755 from the storage unit 75 and displaying the crack depth information 755 on the screen display unit 74. At this time, the crack depth output unit 767 may be configured to display the calculated depth of the crack 61 on image data (or on a displacement distribution for example) which is a target of detecting the crack 61. Furthermore, the crack depth output unit 767 may be configured to display the calculated depth of the crack 61 in different colors depending on the calculated depth of the crack 61.

So far, the configuration of the crack depth evaluation device 7 has been described.

Figure 26:
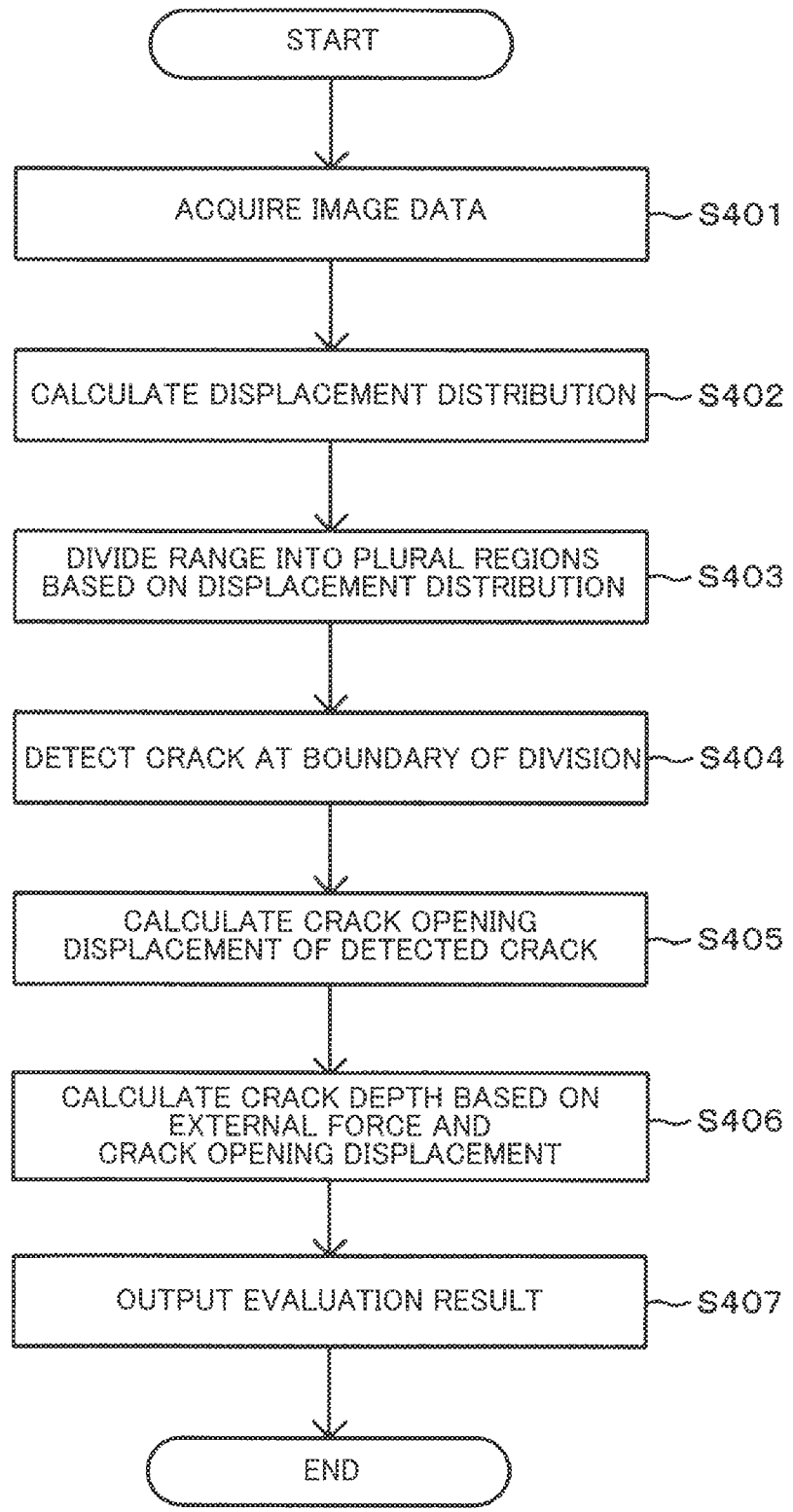
FIG. 26 is a flowchart for explaining an operation of the crack depth evaluation device according to the fifth exemplary embodiment of the present invention.

Next, an operation of the crack depth evaluation device 7 will be described. FIG. 26 is a flowchart illustrating the operation of the crack depth evaluation device 7 according to the present exemplary embodiment. Hereinafter, with reference to FIG. 26, the operation of the crack depth evaluation device 7 will be described. The operations of the crack depth evaluation device 7 from step S401 to step S405 illustrated in FIG. 26 are the same as those from step S201 to step S205 of the structure soundness evaluation device 3 according to the third exemplary embodiment (see FIG. 17). Therefore, hereinafter, the operation of the crack depth evaluation device 7 after step S406 will be described.

As described above, by the operations similar to those of the structure soundness evaluation device 3 according to the third exemplary embodiment, the crack-opening-displacement calculating unit 765 of the crack depth evaluation device 7 calculates a crack opening displacement (step S405). Then, the crack-opening-displacement calculating unit 765 stores the calculated crack opening displacement in the crack-opening-displacement information 754. Furthermore, the external force acquiring unit 77 acquires external force applied to the structure 6 and stores the external force in the external force information 756.

Subsequently, the crack depth calculating unit 766 calculates a crack depth based on the crack opening displacement stored in the crack-opening-displacement information 754 of the storage unit 75 and the applied external force stored in the external force information 756 (step S406). Then, the crack depth calculating unit 766 associates the calculated crack depth with information for identifying the crack 61 from which is a calculation source of the crack width depth displacement, and stores the result as the crack depth information 755.

Thereafter, the crack depth output unit 767 reads the crack depth information 755 of the storage unit 75 and displays the crack depth information 755 on the screen display unit 74 (step S407).

As described above, the crack depth evaluation device 7 according to the present exemplary embodiment has the crack depth calculating unit 766. Furthermore, the crack depth evaluation device 7 stores the external force information 756 acquired from the external force acquiring unit 77. By such a configuration, the crack depth calculating unit 766 can calculate the depth of the detected crack 61 based on the crack opening displacement calculated by the crack-opening-displacement calculating unit 765 and external force applied at that time. As a consequence, the crack depth evaluation device 7 can detect the crack 61 formed on the surface of the structure 6 without erroneously detecting a pattern or the like similar in appearance on an image to the crack 61, and calculate its depth.

Figure 27:
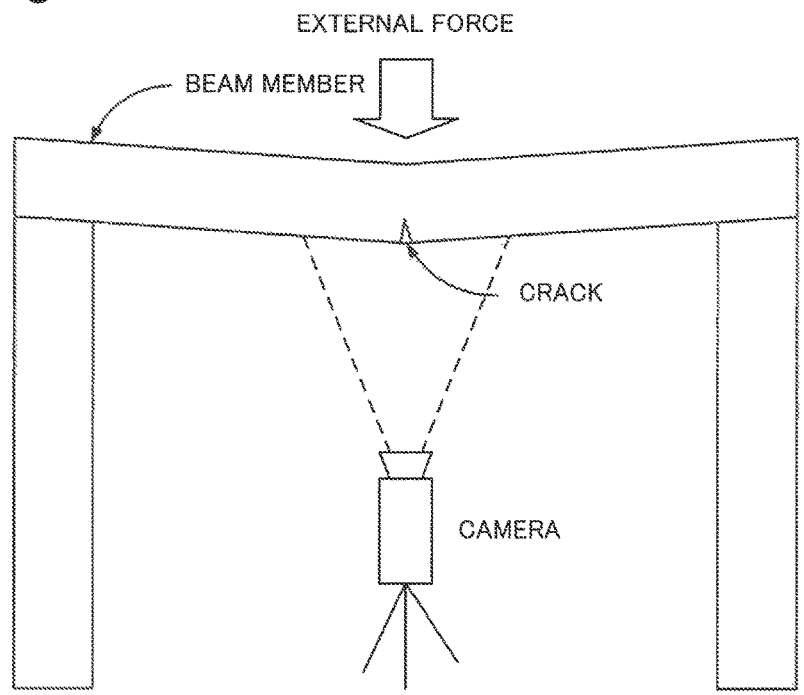
FIG. 27 is a diagram illustrating an example of a configuration of an experimental system using the crack depth evaluation device according to the fifth exemplary embodiment of the present invention.
Figure 28:
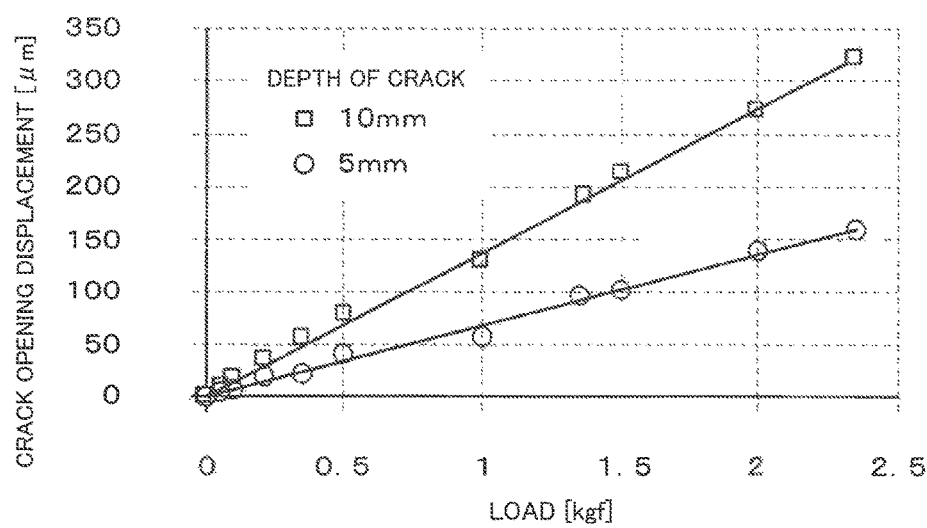
FIG. 28 is a diagram illustrating an example of a relation among a depth of a crack, a crack opening displacement, and a load evaluated by the crack depth evaluation device according to the fifth exemplary embodiment of the present invention.

The following illustrates an example where a relation among a depth of a crack, a crack opening displacement, and a load (external force) is evaluated in a both-end supported experimental system in imitation of a bridge illustrated in FIG. 27 by using the afore-described crack depth evaluation device 7. FIG. 28 is an example of a relation, which is obtained by using the crack depth evaluation device 7, among the depth of a crack, the crack opening displacement, and the load (external force). In the experimental system illustrated in FIG. 27 and FIG. 28, the aforementioned relation is evaluated by using a beam having a length of 200 mm, a width of 100 mm, and a thickness of 30 mm, and made of a polystyrene foam material with a Young's modulus of 14 MPa.

Referring to FIG. 28, it is observed that, when the load F, which is an applied external force, increases twofold, the crack opening displacement $\Delta C$ increases approximately twofold.

Furthermore, in a sample with a crack depth of 5 mm, for example, when the applied load is 2 kgf, the crack opening displacement $\Delta C$ is 138 μm. When the crack depth D is calculated by using these values, the crack depth D is 69/a [μm/kgf]. Furthermore, in a sample with a crack depth of 10 mm, for example, when the applied load is 2 kgf, the crack opening displacement $\Delta C$ is 272 μm. When the crack depth D is calculated by using these values, the crack depth D is 136/a [μm/kgf].

From the above results, when the load F is constant, as the depth of a crack increases approximately twofold, the value of the crack depth D also increases twofold, and a linear relation is confirmed to exist between the crack depth D and the coefficient $\Delta C$, which is proportional to the depth of the crack.

Similarly, when the constant a, which depends on a material and a structure, is calculated from FIG. 28, the constant a is about 0.0136 [kgf] for both crack depths of 5 mm and 10 mm. From the above results, the value of the constant a, which depends on a material and a structure, is confirmed to be approximately constant.

In addition, to the crack depth evaluation device 7 according to the present exemplary embodiment, various changes can be made similar to the changes described with respect to the first to fourth exemplary embodiments.

Next, a sixth exemplary embodiment of the present invention will be described in detail with reference to the drawings.

Sixth Exemplary Embodiment

In the sixth exemplary embodiment, a description will be provided for a structure soundness evaluation device 8 that evaluates the soundness of the structure 6 based on the depth of the crack 61 calculated by the crack depth evaluation device 7 described in the fifth exemplary embodiment.

Figure 29:
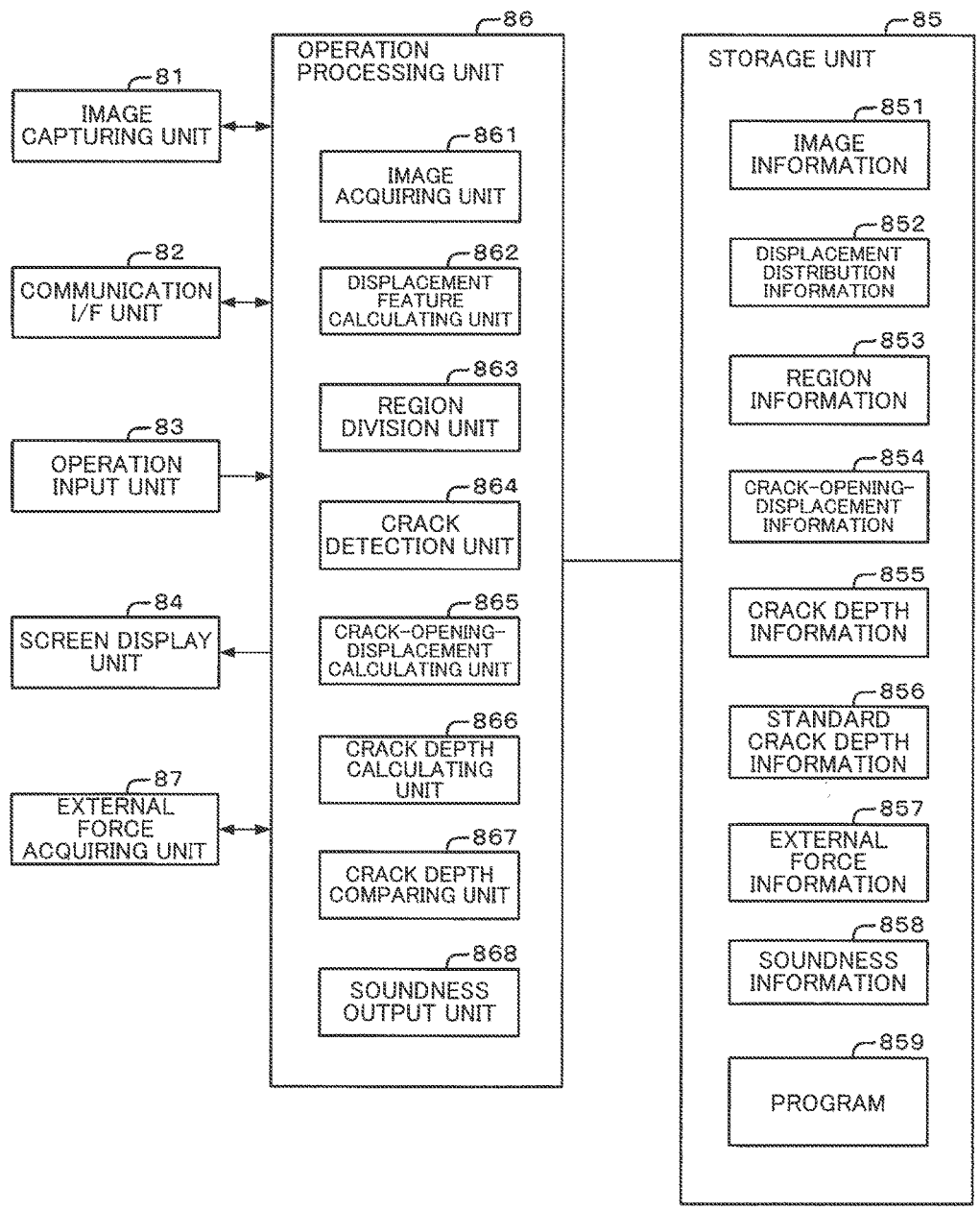
FIG. 29 is a block diagram illustrating a configuration of a structure soundness evaluation device according to a sixth exemplary embodiment of the present invention.

Referring to FIG. 29, the soundness evaluation device 8 according to the present exemplary embodiment has an image capturing unit 81, a communication I/F unit 82, an operation input unit 83, a screen display unit 84, a storage unit 85, an operation processing unit 86, and an external force acquiring unit 87. The image capturing unit 81, the communication I/F unit 82, the operation input unit 83, the screen display unit 84, and the external force acquiring unit 87 have the same functions as those of the image capturing unit 71, the communication I/F unit 72, the operation input unit 73, the screen display unit 74, and the external force acquiring unit 77 of the crack depth evaluation device 7 according to the fifth exemplary embodiment. Therefore, a description thereof will be omitted.

The storage unit 85 is a storage device such as a hard disk and a memory. The storage unit 85 has a function of storing processing information required for various types of processing in the operation processing unit 86 and a program 859. The program 859 is a program which is read and executed by the operation processing unit 86 to realize various processing units. The program 859 is read in advance from an external device (not illustrated) or a storage medium (not illustrated) via a data input/output function of the communication I/F unit 82 and the like, and is stored in the storage unit 85. Main information to be stored in the storage unit 85 includes image information 851, displacement distribution information 852, region information 853, crack-opening-displacement information 854, crack depth information 855, standard crack depth information 856, external force information 857, and soundness information 858. The configurations of the image information 851, the displacement distribution information 852, the region information 853, the crack-opening-displacement information 854, the crack depth information 855, and the external force information 857 are similar to those of the image information 751, the displacement distribution information 752, the region information 753, the crack-opening-displacement information 754, the crack depth information 755, and the external force information 756 of the crack depth evaluation device 7 according to the fifth exemplary embodiment. Therefore, a description thereof will be omitted.

Figure 30:
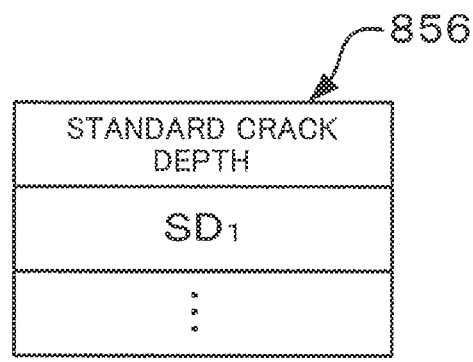
FIG. 30 is a diagram illustrating a configuration example of standard crack depth information in the structure soundness evaluation device according to the sixth exemplary embodiment of the present invention.

The standard crack depth information 856 is information indicating a standard crack depth which is a depth of a crack width used as a standard when evaluating the soundness of the structure 6. The standard crack depth information 856, for example, is inputted in advance via the communication I/F unit 82, the operation input unit 83 or the like, and is stored in the storage unit 85. FIG. 30 is a configuration example of the standard crack depth information 856. Referring to FIG. 30, the standard crack depth information 856 stores the standard crack depth used as a standard when evaluating the soundness of the structure 6. For example, the first row of FIG. 30 indicates that the standard crack depth is SD1. In addition, the standard crack depth information 756 may include a plurality of standard crack depths.

The soundness information 858 is information calculated based on the crack depth (see FIG. 25) and the standard crack depth (see FIG. 30) and indicating the soundness of the structure 6. Even though the based information at the time of calculation is different, the configuration example of the soundness information 858 is the same as that of the soundness information 356 illustrated in FIG. 16. Therefore, details of the soundness information 858 will be omitted.

The operation processing unit 86 has a microprocessor such as a MPU and a peripheral circuit thereof, and has a function of making the aforementioned hardware and the program 859 cooperate with each other, and implementing various processing units, by reading the program 859 from the storage unit 85 to execute it. Main processing units implemented by the operation processing unit 86 include an image acquiring unit 861, a displacement feature calculating unit 862, a region division unit 863, a crack detection unit 864, a crack-opening-displacement calculating unit 865, a crack depth calculating unit 866, a crack depth comparing unit 867 (a second soundness evaluating means), and a soundness output unit 868. The configurations of the image acquiring unit 861, the displacement feature calculating unit 862, the region division unit 863, the crack detection unit 864, the crack-opening-displacement calculating unit 865, and the crack depth calculating unit 866 are similar to those of the image acquiring unit 761, the displacement feature calculating unit 762, the region division unit 763, the crack detection unit 764, the crack-opening-displacement calculating unit 765, and the crack depth calculating unit 766 of the crack depth evaluation device 7 according to the fifth exemplary embodiment. Therefore, a description thereof will be omitted.

The crack depth comparing unit 867 has a function of reading the crack depth information 855 and the standard crack depth information 856 from the storage unit 85, and evaluating the soundness of the structure 6 based on the read crack depth information 855 and the read standard crack depth information 856. For example, the crack depth comparing unit 867 reads "10 mm" as the crack depth D1. Furthermore, the crack depth comparing unit 867 reads "5 mm" as the standard crack depth $SD_1$. Then, the crack depth comparing unit 867 compares the crack depth D1 with the standard crack depth $SD_1$. In this case, the crack depth D1 is larger than the standard crack depth $SD_1$. Therefore, the crack depth comparing unit 867 determines that the soundness of the structure 6 is bad for example.

Thereafter, the crack depth comparing unit 867 associates the soundness, which is obtained by comparing the crack depth with the standard crack depth, with a structure identification ID for identifying the structure 6 (having the crack 61) which is a target of determining the soundness, and stores the result in the storage unit 85 as the soundness information 858.

In addition, when a plurality of standard crack depths are included in the standard crack depth information 856, the crack depth comparing unit 867 may be configured to evaluate the soundness on a scale by making comparison by using respective standard crack depths as threshold values.

The soundness output unit 868 has a function of reading the soundness information 858 from the storage unit 85 and displaying the soundness information 858 on the screen display unit 84. For example, the soundness output unit 868 also reads a corresponding displacement distribution from the displacement distribution information 852, thereby displaying the soundness superimposed on the displacement distribution on the screen display unit 84.

So far, the configuration of the structure soundness evaluation device 8 has been described.

Figure 31:
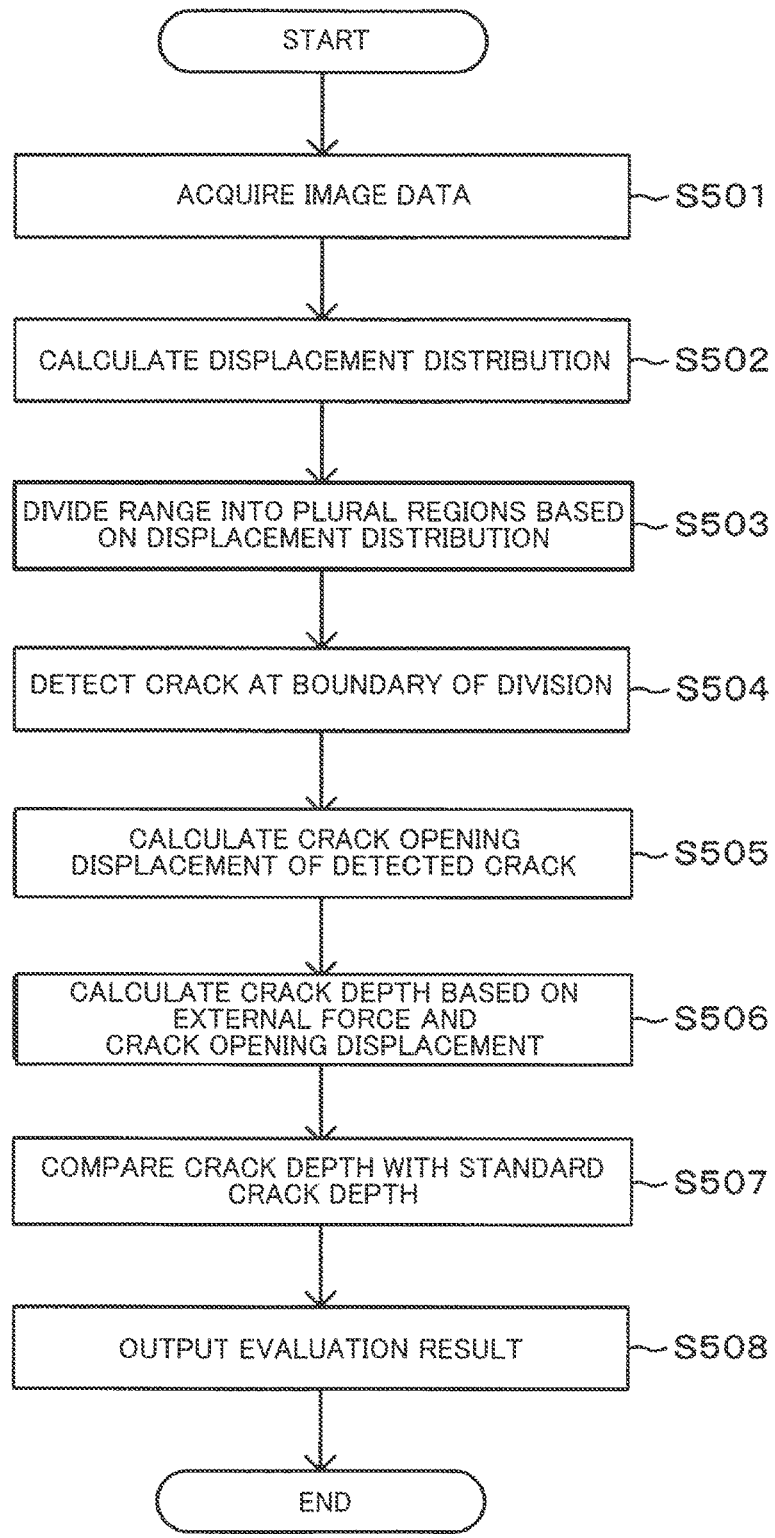
FIG. 31 is a flowchart for explaining an operation of the structure soundness evaluation device according to the sixth exemplary embodiment of the present invention.

Next, an operation of the structure soundness evaluation device 8 will be described. FIG. 31 is a flowchart illustrating the operation of the structure soundness evaluation device 8 according to the present exemplary embodiment. Hereinafter, with reference to FIG. 31, the operation of the structure soundness evaluation device 8 will be described. The operations of the structure soundness evaluation device 8 from step S501 to step S506 illustrated in FIG. 31 are the same as those from step S401 to step S406 of the crack depth evaluation device 7 according to the fifth exemplary embodiment (see FIG. 26). Therefore, hereinafter, the operation of the structure soundness evaluation device 8 after step S507 will be described.

As described above, by the operations similar to those of the crack depth evaluation device 7 according to the fifth exemplary embodiment, the crack depth calculating unit 866 of the structure soundness evaluation device 8 calculates the depth of the crack 61 (step S506). Then, the crack depth calculating unit 866 stores the calculation result in the crack depth information 855.

Subsequently, the crack depth comparing unit 867 compares the crack depth stored in the crack depth information 855 of the storage unit 85 with the standard crack depth stored in the standard crack depth information 856 (step S507), and evaluates the soundness of the structure 6. Then, the crack depth comparing unit 867 stores the evaluation result in the soundness information 858.

Thereafter, the soundness output unit 868 reads the soundness information 858 of the storage unit 85 and displays the read soundness information 858 on the screen display unit 34 (step S508).

As described above, the structure soundness evaluation device 8 according to the present exemplary embodiment has the crack depth comparing unit 867. Furthermore, the structure soundness evaluation device 8 stores the standard crack depth information 856. By such a configuration, the crack depth comparing unit 867 can compare the crack depth calculated by the crack depth calculating unit 866 with the standard crack depth, thereby evaluating the soundness of the structure 6. As described above, the structure soundness evaluation device 8 according to the present exemplary embodiment can detect the crack 61 formed on the surface of the structure 6 without erroneously detecting a pattern or the like similar in appearance on an image to the crack 61. Therefore, by evaluating the soundness of the structure 6 based on the crack depth of the detected crack 61, it is possible to more accurately evaluate the soundness of the structure 6.

In addition, to the structure soundness evaluation device 8 according to the present exemplary embodiment, various changes can be made similar to the changes described with respect to the first to fifth exemplary embodiments.

Seventh Exemplary Embodiment

In the seventh exemplary embodiment, a description will be provided for a crack detection device 5 that detects a crack 61 formed on the structure 6 based on a temporal position change of at least two measurement points. In the present exemplary embodiment, the outline of the configuration of the crack detection device 5 will be described.

Figure 32:
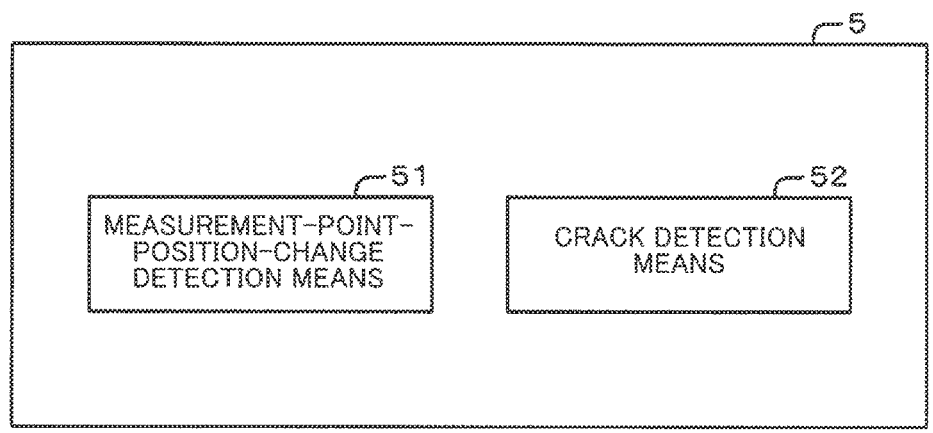
FIG. 32 is a block diagram illustrating an outline of a configuration of a crack detection device according to a seventh exemplary embodiment of the present invention.

Referring to FIG. 32, the crack detection device 5 according to the present exemplary embodiment has measurement-point-position-change detection means 51 and crack detection means 52.

The measurement-point-position-change detection means 51 has a function of detecting a temporal position change of at least two measurement points on the structure 6. As described above, the measurement-point-position-change detection means 51 detects a temporal position change of at least two measurement points on the structure 6. Then, the measurement-point-position-change detection means 51 notifies the crack detection means 52 of the detection result.

The crack detection means 52 has a function of detecting the crack 61 based on the change in the positions of the respective measurement points detected by the measurement-point-position-change detection means 51. The crack detection means 52 receives the detection result notification from the measurement-point-position-change detection means 51. Then, the crack detection means 52 detects the crack 61 based on the received detection result.

As described above, the crack detection device 5 according to the present exemplary embodiment includes the measurement-point-position-change detection means 51 and the crack detection means 52. By such a configuration, the crack detection device 5 can detect the crack 61 based on the detection result by the measurement-point-position-change detection means 51. In general, the width of the crack 61 is changed by various influences. Therefore, a temporal position change of measurement points is affected by a change in the width of the crack 61. In contrast, a pattern or the like that appear similar on image does not have such features. Therefore, by detecting the crack 61 based on a temporal position change of measurement points, it is possible to detect the crack 61 formed on the surface of the structure 6 without erroneously detecting a pattern or the like similar in appearance on an image to the crack 61.

<Supplementary Note>

The whole or part of the exemplary embodiments disclosed above can be described as. Hereinafter, such as summaries of the crack detecting device of the present invention will be described. However, the present invention does not limited to the following constitutions.

(Supplementary Note 1)

An information processing device that detects a crack on a structure, includes:

a change detection unit that detects a change in positions of at least two measurement points on the structure; and a crack detection unit that detects a crack based on the change in the positions of the measurement points detected by the change detection unit.

(Supplementary Note 2)

The information processing device according to supplementary note 1, wherein the crack detection unit detects that there is the crack between the two measurement points based on a relation of the change in the positions of the two measurement points on the structure.

(Supplementary Note 3)

The information processing device according to supplementary note 2, wherein the crack detection unit detects that there is the crack between the two measurement points when the change in the positions of the two measurement points satisfies a predetermined condition.

(Supplementary Note 4)

The information processing device according to any one of supplementary notes 1 to 3, wherein the crack detection unit detects that there is the crack between the two measurement points based on a relation of the change in the positions of the two measurement points and a relation of a change in positions of measurement points around the two measurement points.

(Supplementary Note 5)

The information processing device according to any one of supplementary notes 1 to 4, further includes:

a crack-opening-displacement calculating unit that calculates a crack opening displacement, which is a displacement of a crack opening of the crack detected by the crack detection unit, based on the change in the positions of the measurement points.

(Supplementary Note 6)

The information processing device according to supplementary note 5, wherein the crack-opening-displacement calculating unit calculates, as the crack opening displacement, a maximal value of the displacement of the crack opening of the crack detected by the crack detection unit.

(Supplementary Note 7)

The information processing device according to supplementary note 5 or 6, further includes:

a first soundness evaluating unit that evaluates soundness of a target structure based on the crack opening displacement calculated by the crack-opening-displacement calculating unit.

(Supplementary Note 8)

The information processing device according to supplementary note 7, wherein the first soundness evaluating unit comprises:

a standard crack-opening-displacement storing unit that stores a standard crack opening displacement as a standard of soundness evaluation; and a crack-opening-displacement comparing unit that compares the crack opening displacement calculated by the crack-opening-displacement calculating unit with the standard crack opening displacement stored in the standard crack-opening-displacement storing unit, wherein the soundness of the target structure is evaluated based on the comparison result by the crack-opening-displacement comparing unit.

(Supplementary Note 9)

The information processing device according to supplementary note 8, further includes:

an external force acquiring unit that acquires external force applied to the structure having the crack detected by the crack detection unit; and an estimating unit that estimates a crack opening displacement at standard external force, which is a crack opening displacement when external force used as a standard in soundness evaluation is applied, based on the external force at a time of calculation of the crack opening displacement, which has been acquired by the external force acquiring unit, and the crack opening displacement, wherein the first soundness evaluating unit evaluates the soundness of the target structure based on a comparison result of the crack opening displacement at standard external force and the standard crack opening displacement.

(Supplementary Note 10)

The information processing device according to any one of supplementary notes 5 to 9, further includes:

an image data acquiring unit that acquires image data indicating the structure that is a target for checking a crack; and a crack width calculating unit that calculates the crack width of the crack detected by the crack detection unit, based on image data in which the crack opening displacement calculated by the crack-opening-displacement calculating unit is maximal.

(Supplementary Note 11)

The information processing device according to any one of supplementary notes 5 to 10, further includes:

an external force acquiring unit that acquires external force applied to the structure having the crack detected by the crack detection unit; and a crack depth calculating unit that calculates a depth of the crack detected by the crack detection unit, based on the external force at the time of the calculation of the crack opening displacement acquired by the external force acquiring unit, and the crack opening displacement.

(Supplementary Note 12)

The information processing device according to supplementary note 11, further includes:

a second soundness evaluating unit that evaluates the soundness of the target structure based on the depth of the crack detected by the crack depth calculating unit.

(Supplementary Note 13)

The information processing device according to supplementary note 12, wherein the second soundness evaluating unit evaluates the soundness of the target structure based on a result of comparison the depth of the crack calculated by the crack depth calculating unit with a standard crack depth which is a depth of a crack used as a standard of soundness evaluation.

(Supplementary Note 14)

The information processing device according to any one of supplementary notes 1 to 13, wherein the change detection unit detects the change in the positions of at least two measurement points on the structure before and after predetermined external force is applied, and the crack detection unit detects the crack based on the change in each of the positions of the measurement points on the structure before and after the predetermined external force is applied.

(Supplementary Note 15)

The information processing device according to any one of supplementary notes 1 to 14, wherein the change detection unit detects at least one of a displacement direction or a displacement quantity of the measurement points as the change in the positions of the measurement points, and the crack detection unit detects the crack based on at least one of the displacement direction or the displacement quantity at each measurement point, which are detected by the change detection unit.

(Supplementary Note 16)

16. The information processing device according to any one of supplementary notes 1 to 15, wherein the change detection unit calculates a displacement distribution, which indicates a distribution of the change in the positions of the measurement points, and the crack detection unit divides the displacement distribution into a plurality of regions based on the proximity of the change in the positions of the measurement points, and detects that there is a crack at a boundary between divided regions based on a change in positions of each of divided regions.

(Supplementary Note 17)

The information processing device according to supplementary note 16, wherein the crack detection unit divides the displacement distribution into a plurality of regions such that regions in which the change satisfies a predetermined condition are consolidated, and detects that there is a crack at the boundary between the divided regions.

(Supplementary Note 18)

An information processing method that detects a crack on a structure, includes:

detecting a change in positions of at least two measurement points on the structure; and detecting a crack based on the detected change in the positions of the measurement points.

(Supplementary Note 18-1)

The information processing method according to supplementary note 18, wherein detecting the crack is detecting that there is the crack between the two measurement points based on a relation of the change in the positions of the two measurement points on the structure.

(Supplementary Note 18-2)

The information processing method according to supplementary note 18 or 18-1, wherein detecting the crack is detecting that there is the crack between the two measurement points based on a relation of the change in the positions of the two measurement points and a relation of a change in positions of measurement points around the two measurement points.

(Supplementary Note 18-3)

The information processing method according to supplementary note 18-2, wherein detecting the crack is detecting that there is the crack between the two measurement points when the change in the positions of the two measurement points satisfies a predetermined condition.

(Supplementary Note 19)

A computer readable non-transitory medium embodying a program, the program causing:

detecting a change in positions of at least two measurement points on a structure; and detecting a crack based on the detected change in the positions of the measurement points.

(Supplementary Note 19-1)

The program according to supplementary note 19, wherein the method detecting the crack is detecting that there is the crack between the two measurement points based on a relation of the change in the positions of the two measurement points on the structure.

(Supplementary Note 19-2)

The program according to supplementary notes 19 or 19-1, wherein the method detecting the crack is detecting that there is the crack between the two measurement points based on a relation of the change in the positions of the two measurement points and a relation of a change in positions of measurement points around the two measurement points.

(Supplementary Note 19-3)

The program according to supplementary note 19-2, wherein the method detecting the crack is detecting that there is the crack between the two measurement points when the change in the positions of the two measurement points satisfies a predetermined condition.

In addition, the program described in the aforementioned exemplary embodiments and supplementary notes is stored in a storage device or is recorded on a computer readable recording medium. For example, the recording medium is a portable medium such as a flexible disk, an optical disk, a magneto-optic disk, and a semiconductor memory.

As above-mentioned, while the invention has been particularly shown and described with reference to each of exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2014-085029, filed on Apr. 16, 2014, the disclosure of which is incorporated herein in its entirety by reference.

REFERENCE SINGS LIST 1, 2 crack detection device
11, 21, 31, 41 image capturing unit
12, 22, 32, 42 communication I/F unit
13, 23, 33, 43 operation input unit
14, 24, 34, 44 screen display unit
15, 25, 35, 45 storage unit
151, 251, 351, 451 image information
152 displacement feature information
153, 254, 357, 459 program
16, 26, 36, 46 operation processing unit
161, 261, 361, 461 image acquiring unit
162, 262, 362, 462 displacement feature calculating unit
163, 264, 364, 464 crack detection unit
252, 352, 452 displacement distribution information
253, 353, 453 region information
263, 363, 463 region division unit
3, 4 structure soundness evaluation device
354, 454 crack-opening-displacement information
355, 455 standard crack-opening-displacement information
356, 458 soundness information
365, 465 crack-opening-displacement calculating unit
366, 466 crack-opening-displacement comparing unit
367, 468 soundness output unit
368 crack width calculating unit
456 external force information
457 crack-opening-displacement-at-standard-external-force information
467 crack-opening-displacement-at-standard-external-force calculating unit
47 external force acquiring unit
5 crack detection device
51 measurement-point-position-change detection means
52 crack detection means
6 structure
61 crack
7 crack depth evaluation unit
8 soundness evaluation device
71, 81 image capturing unit
72, 82 communication I/F unit
73, 83 operation input unit
74, 84 screen display unit
75, 85 storage unit
751, 851 image information
752, 852 displacement distribution information
753, 853 region information
754, 854 crack-opening-displacement information
755, 855 crack depth information
856 standard crack depth information
756, 857 external force information
858 soundness information
757, 859 program
76, 86 operation processing unit
761, 861 image acquiring unit
762, 862 displacement feature calculating unit
763, 863 region division unit
764, 864 crack detection unit

765, 865 crack-opening-displacement calculating unit
766, 866 crack depth calculating unit
767 crack depth output unit
867 crack depth comparing unit
868 soundness output unit

The invention claimed is:

1. An information processing device configured to detect a crack on a structure, comprising:
   a memory storing a program; and
   a processor configured to execute the program to:
      receive image data corresponding to images of the structure acquired at different times;
      calculate displacement features of at least two arbitrary regions in the image data, each displacement feature indicating a temporal change in position of an arbitrary region in the image data corresponding to an arbitrary measurement point on the structure;
      compare the displacement features for the at least two arbitrary regions to detect at least one of a location or an existence of the crack in the structure;
      calculate a displacement distribution, which indicates a distribution of the change in the positions of the at least two arbitrary regions; and
      divide the displacement distribution into a plurality of regions based on the proximity of the change in the positions of the at least two arbitrary regions, and detect that the location of the crack is at a boundary between divided regions.

2. The information processing device according to claim 1, wherein the processor is further configured to execute the program to:
   detect that the crack is located between a first measurement point in a first arbitrary region and a second measurement point in a second arbitrary region based on a relation between the displacement features for the first and second arbitrary regions.

3. The information processing device according to claim 2, wherein the processor is further configured to execute the program to:
   detect that there is the crack between the first and second measurement points when the relation between the displacement features satisfies a predetermined condition.

4. The information processing device according to claim 2, wherein the processor is further configured to execute the program to:
   detect that there is the crack between the first and second measurement points based on a relation of the displacement features of the first and second arbitrary regions and a relation of a change in positions of measurement points around the first and second measurement points.

5. The information processing device according to claim 1, wherein the processor is further configured to execute the program to:
   calculate a crack opening displacement, which is a displacement of a crack opening of the detected crack, based on the displacement features.

6. The information processing device according to claim 5, wherein the processor is further configured to execute the program to:
   calculate, as the crack opening displacement, a maximal value of the displacement of the crack opening of the detected crack.

7. The information processing device according to claim 5, wherein the processor is further configured to execute the program to:
   evaluate soundness of the structure based on the calculated crack opening displacement.

8. The information processing device according to claim 7, wherein the processor is further configured to execute the program to:
   store, in the memory, a standard crack opening displacement as a standard of soundness evaluation;
   compare the calculated crack opening displacement with the standard crack opening displacement; and
   evaluate the soundness of the structure based on the comparison result.

9. The information processing device according to claim 8, wherein the processor is further configured to execute the program to:
   acquire external force applied to the structure having the detected crack;
   estimate a crack opening displacement at standard external force, which is a crack opening displacement when external force used as a standard in soundness evaluation is applied, based on the external force acquired at a time of calculation of the crack opening displacement, and the crack opening displacement; and
   evaluate the soundness of the structure based on a comparison result of the crack opening displacement at standard external force and the standard crack opening displacement.

10. The information processing device according to claim 5, wherein the processor is further configured to execute the program to:
    acquire additional image data indicating the structure that is a target for checking for cracks; and
    calculate the crack width of the detected crack, based on the additional image data in which the calculated crack opening displacement is maximal.

11. The information processing device according to claim 5, wherein the processor is further configured to execute the program to:
    acquire external force applied to the structure having the detected crack; and
    calculate a depth of the detected crack, based on the external force acquired at the time of the calculation of the crack opening displacement, and the crack opening displacement.

12. The information processing device according to claim 11, wherein the processor is further configured to execute the program to:
    evaluate the soundness of the structure based on the calculated depth of the crack.

13. The information processing device according to claim 12, wherein the processor is further configured to execute the program to:
    evaluate the soundness of the structure based on a result of comparison of the calculated depth of the crack with a standard crack depth representing a standard of soundness evaluation.

14. The information processing device according to claim 1, wherein the processor is further configured to execute the program to:
    calculate the displacement features before and after a predetermined external force is applied, and
    detect the crack based on the displacement features before and after the predetermined external force is applied.

15. The information processing device according to claim 1, wherein
    the displacement features include at least one of a displacement direction and a displacement quantity, and the processor is further configured to execute the program to detect the existence or location of the crack based on at least one of the displacement direction or the displacement quantity.

16. The information processing device according to claim 1, wherein the processor is further configured to execute the program to:
divide the displacement distribution into the plurality of regions such that regions in which the change satisfies a predetermined condition are consolidated.

17. An information processing method for detecting a crack on a structure, comprising:
receiving image data corresponding to images of the structure acquired at different times;
calculating displacement features of at least two arbitrary regions in the image data, each displacement feature indicating a temporal change in position of an arbitrary region in the image data corresponding to an arbitrary measurement point on the structure;
comparing the displacement features for the at least two arbitrary regions to detect at least one of a location or an existence of the crack in the structure;
calculating a displacement distribution, which indicates a distribution of the change in the positions of the at least two arbitrary regions; and
dividing the displacement distribution into a plurality of regions based on the proximity of the change in the positions of the at least two arbitrary regions, and detect that the location of the crack is at a boundary between divided regions.

18. A computer readable non-transitory medium storing a program that, when executed by a computer, causes the computer to perform a method, the method comprising:
receiving image data corresponding to images of the structure acquired at different times;
calculating displacement features of at least two arbitrary regions in the image data, each displacement feature indicating a temporal change in position of an arbitrary region in the image data corresponding to an arbitrary measurement point on the structure;
comparing the displacement features for the at least two arbitrary regions to detect at least one of a location or an existence of the crack in the structure;
calculating a displacement distribution, which indicates a distribution of the change in the positions of the at least two arbitrary regions; and
dividing the displacement distribution into a plurality of regions based on the proximity of the change in the positions of the at least two arbitrary regions, and detect that the location of the crack is at a boundary between divided regions.

19. An information processing device configured to detect a crack on a structure, comprising:
at least one processor configured to execute machine-readable instructions to implement:
a change detection means configured to calculate displacement features of at least two arbitrary regions in image data of the structure acquired at different times, each displacement feature indicating a temporal change in position of an arbitrary region in the image data corresponding to an arbitrary measurement point on the structure; and
a crack detection means configured to detect at least one of a location or an existence of the crack based on a comparison of the displacement features for the at least two arbitrary regions, to calculate a displacement distribution, which indicates a distribution of the change in the positions of the at least two arbitrary regions, and to divide the displacement distribution into a plurality of regions based on the proximity of the change in the positions of the at least two arbitrary regions, and detect that the location of the crack is at a boundary between divided regions.

20. The information processing device of claim 1, wherein each displacement feature includes a displacement direction and a displacement quantity.

* * * * *